(12) United States Patent
Kim et al.

(10) Patent No.: US 10,874,854 B2
(45) Date of Patent: Dec. 29, 2020

(54) MESH ELECTRODE FOR CARDIAC RESYNCHRONIZATION THERAPY, AND MANUFACTURING METHOD THEREFOR

(71) Applicants: Seoul National University R&DB Foundation, Seoul (KR); INSTITUTE FOR BASIC SCIENCE, Daejeon (KR)

(72) Inventors: Dae-Hyeong Kim, Incheon (KR); Taeghwan Hyeon, Seoul (KR); Hye Jin Hwang, Seoul (KR); Jinkyung Park, Seoul (KR); Suji Choi, Seoul (KR)

(73) Assignees: Seoul National University R&DB Foundation, Seoul (KR); INSTITUTE FOR BASIC SCIENCE, Daejeon (KR)

( * ) Notice: Subject to any disclaimer, the term of this patent is extended or adjusted under 35 U.S.C. 154(b) by 420 days.

(21) Appl. No.: 15/525,277

(22) PCT Filed: Mar. 31, 2015

(86) PCT No.: PCT/KR2015/003211
§ 371 (c)(1),
(2) Date: May 8, 2017

(87) PCT Pub. No.: WO2016/076485
PCT Pub. Date: May 19, 2016

(65) Prior Publication Data
US 2018/0280690 A1   Oct. 4, 2018

(30) Foreign Application Priority Data

Nov. 11, 2014   (KR) .................. 10-2014-0156309

(51) Int. Cl.
*A61N 1/05*   (2006.01)
*A61L 31/02*   (2006.01)
(Continued)

(52) U.S. Cl.
CPC .......... *A61N 1/0597* (2013.01); *A61L 31/022* (2013.01); *A61L 31/041* (2013.01);
(Continued)

(58) Field of Classification Search
CPC ....... A61N 1/0597; A61N 1/05; A61L 31/146; A61L 31/022; A61L 31/041; A61L 31/14;
(Continued)

(56) References Cited

U.S. PATENT DOCUMENTS 7,181,272 B2   2/2007   Struble et al.
7,587,238 B2   9/2009   Moffitt et al.
(Continued)

FOREIGN PATENT DOCUMENTS

WO   WO 2008/024857 A2   2/2008

OTHER PUBLICATIONS

International Search Report for International Patent Application No. PCT/KR2015/003211 filed on Mar. 31, 2015.

*Primary Examiner* — Christopher Koharski
*Assistant Examiner* — James Moss

(57) ABSTRACT

The present invention relates to a mesh electrode for cardiac resynchronization therapy, and a manufacturing method therefor. More specifically, the present invention relates to: a mesh electrode for cardiac resynchronization therapy, formed from a wire composed of a first biocompatible rubber layer in which silver nanowires are dispersed, and a second biocompatible rubber layer famed so as to be adjacent to the first biocompatible rubber layer; and a manufacturing method therefor.

7 Claims, 30 Drawing Sheets

(51) Int. Cl.
*A61L 31/04* (2006.01)
*A61L 31/14* (2006.01)
*B29C 39/10* (2006.01)
*B29K 505/14* (2006.01)
*B29L 31/34* (2006.01)

(52) U.S. Cl.
CPC ............. *A61L 31/14* (2013.01); *A61L 31/146* (2013.01); *A61N 1/05* (2013.01); *B29C 39/10* (2013.01); *A61L 2400/12* (2013.01); *B29K 2505/14* (2013.01); *B29K 2995/0056* (2013.01); *B29L 2031/34* (2013.01)

(58) Field of Classification Search
CPC . A61L 2400/12; B29C 39/10; B29L 2031/34; B29K 2505/14; B29K 2995/0056
See application file for complete search history.

(56) References Cited

U.S. PATENT DOCUMENTS

| | | | | |
|---|---|---|---|---|
| 2003/0199955 A1* | 10/2003 | Struble | ................ | A61N 1/0597 607/119 |
| 2007/0043416 A1* | 2/2007 | Callas | ................ | A61N 1/0597 607/129 |
| 2012/0065703 A1* | 3/2012 | Paukshto | ............. | A61L 27/446 607/50 |
| 2012/0157804 A1* | 6/2012 | Rogers | ................ | A61B 5/0422 600/345 |
| 2015/0037517 A1* | 2/2015 | Buriak | ................. | B05D 1/005 427/600 |

* cited by examiner

MeshP in post-MI

SR in post-MI

MESH ELECTRODE FOR CARDIAC RESYNCHRONIZATION THERAPY, AND MANUFACTURING METHOD THEREFOR

CROSS-REFERENCE TO RELATED APPLICATIONS

The present specification is a U.S. National Stage of International Patent Application No. PCT/KR2015/003211 filed Mar. 31, 2015, which claims priority to and the benefit of Korean Patent Application No. 10-2014-0156309 filed in the Korean Intellectual Property Office on Nov. 11, 2014 the entire contents of which are incorporated herein by reference.

TECHNICAL FIELD

The present invention relates to a mesh electrode for cardiac resynchronization therapy and a manufacturing method therefor. More specifically, the present invention relates to a mesh electrode for cardiac resynchronization therapy famed from a wire comprising a first biocompatible rubber layer in which silver nanowires are dispersed and a second biocompatible rubber layer formed adjacent to the first biocompatible rubber layer, and a manufacturing method therefor.

BACKGROUND ART

In America, heart failure shows a 5-year mortality rate higher than that of most cancers (Askoxylakis, V. et al. Long-term survival of cancer patients compared to heart failure and stroke: A systematic review. BMC Cancer 10, 105-105 (2010), Stewart, S. et al. Population impact of heart failure and the most common forms of cancer: A study of 1 162 309 hospital cases in sweden (1988 to 2004). Circ. Cardiovasc. Qual. Outcomes 3, 573-580 (2010)), and is the major cause of death and morbidity rates (Murphy, S. L., Xu, J. & Kochanek, K. D. Deaths: Final data for 2010. Natl. Vital Stat. Rep. 61, 1-117 (2013)). Attempts to improve cardiac functions, decrease arrhythmia and increase a survival rate have been made through a number of basic and clinical researches. Clinical trials for new pharmacological and regenerative therapy are being made, but drugs to delay the natural course of heart failure are rare (Yancy, C. W. et al. 2013 accf/aha guideline for the management of heart failure: A report of the american college of cardiology foundation/american heart association task force on practice guidelines. Circulation 128, e240-327 (2013)). Regenerative therapy using stem cells or tissue engineering technology receives huge attention and has been developed for dozens of years, but there remains a problem that it is difficult to replace the diseased myocardia with healthy myocardium cells with high durability.

Unlike a pharmacological substance and regenerative therapy, clinical trials proved that only the biventricular pacing that improves long-tem survival as well as cardiac function and symptom quickly is a remedy for heart failure (Moss, A. J. et al. Cardiac-resynchronization therapy for the prevention of heart-failure events. N. Engl. J. Med. 361, 1329-1338 (2009), Tang, A. S. L. et al. Cardiac-resynchronization therapy for mild-to-moderate heart failure. N. Engl. J. Med. 363, 2385-2395 (2010), Goldenberg, I. et al. Survival with cardiac-resynchronization therapy in mild heart failure. N. Engl. J. Med. 370, 1694-1701 (2014)). It is considered that advantageous effects are due to local and global molecules remodeling that includes the improvement of $Ca^{2+}$ sensitivity of myofilament, homogeneous activation of stress kinase and the decrease of apoptotic signal (Neubauer, S. & Redwood, C. New mechanisms and concepts for cardiac-resynchronization therapy. N. Engl. J. Med. 370, 1164-1166 (2014), Chakir, K. et al. Reversal of global apoptosis and regional stress kinase activation by cardiac resynchronization. Circulation 117, 1369-1377 (2008)).

Despite these positive data, electrical current sources generated from only two electrodes located in the dilated ventricle are too small to completely restore synchronous contraction that maximizes the pumping of the heart. Clinical study shows that QRS duration on surface electrogram is amended incompletely by biventricular pacing, and this reminds us of the necessity of completely synchronized electric depolarization and subsequent completely synchronized mechanical contraction.

Myocardial disease in heart failure involves the bulk of specialized conductive system and damage or injury for a myocardium, and this leads to pump failure and activates harmful neurohormonal response and cellular signaling cascade (Josephson Mark, E. Intraventricular conduction disturbances. in Clinical cardiac electrophysiology: Techniques and interpretations (Wolters Kluwer Health/Lippincott Williams & Wilkins, 2008)). Therefore, therapeutic approach that makes a partial compensation for damaged myocardium and replaces the function of diseased His-Purkinje system can be a promising therapeutic method.

Here, we, inventors introduce global resynchronization therapy that uses an epicardial mesh fabricated by designing electrical conductivity and elastic materials in two tactical approaches. First, we fabricated an epicardium-like substrate that is integrated with a heart and shares a load to reduce internal myocardial wall stress. Second, we injected His-Purkinje fiber network function into the epicardium-like device through the global pacing.

DISCLOSURE

Technical Problem

The basic object of the present invention is to provide a mesh electrode for cardiac resynchronization therapy, formed from a wire comprising a first biocompatible rubber layer in which silver nanowires are dispersed and a second biocompatible rubber layer formed adjacent to the first biocompatible rubber layer.

Another object of the present invention is to provide a manufacturing method of a mesh electrode for cardiac resynchronization therapy comprising (i) forming a first biocompatible rubber layer by pouring a first biocompatible rubber solution in which silver nanowires are dispersed into a mold and drying the rubber solution and (ii) forming a second biocompatible rubber layer on the first biocompatible rubber layer.

Technical Solution

The basic object of the present invention can be achieved by providing a mesh electrode for cardiac resynchronization therapy, formed from a wire comprising a first biocompatible rubber layer in which silver nanowires are dispersed and a second biocompatible rubber layer formed adjacent to the first biocompatible rubber layer.

In one embodiment of the present invention, the mesh electrode may have a serpentine structure so that it can be extended according to heartbeats. In addition, the modulus of the entire mesh electrode can be adjusted by changing the serpentine shape and the radius of curvature.

In the mesh electrode according to the present invention, a length of the silver nanowires may range from about 5 μm to about 50 μm, and a diameter of the silver nanowires may range from about 50 nm to about 150 nm. In addition, the silver nanowires may be ligand-exchanged silver nanowires. The ligand may be substituted by alkyl amine, alkyl carboxylic acid, alkyl thiol group, and the ligand with the alkyl structure can make silver nanowires and organic dispersed elastic polymer such as SBS (styrene-butadiene-styrene) and PDMS (polydimethylsiloxane) dispersed uniformly.

In the mesh electrode according to the present invention, the first biocompatible rubber may be selected from a group consisting of SBS rubber, TPU (theLmoplastic polyurethane), NBR (nitrile butadiene rubber), Hydrogel, PDMS, PUA (polyurethane acrylate), PVA (polyvinyl alcohol), Ecoflex®, PI (polyimide), PMMA (polymethyl methacrylate), PVDF (poly(vinylidenedifluoride)). In addition, a thickness of the first biocompatible rubber layer may range from about 1 μm to about 500 μm.

In the mesh electrode according to the present invention, the second biocompatible rubber may be selected from a group consisting of SBS rubber, TPU, NBR, Hydrogel, PDMS, PUA, PVA, Ecoflex®, PI, PMMA, PVDF. In addition, a thickness of the second biocompatible rubber layer may range from about 1 μm to about 500 μm.

Another object of the present invention can be achieved by providing a manufacturing method of a mesh electrode for cardiac resynchronization therapy comprising (i) forming a first biocompatible rubber layer by pouring a first biocompatible rubber solution in which silver nanowires are dispersed into a mold and drying the rubber solution and (ii) forming a second biocompatible rubber layer on the first biocompatible rubber layer.

In one embodiment of the present invention, in order to fabricate the mesh electrode, a PDMS mold in which a mesh shape is engraved in intaglio may be used. Nanocomposite of silver nanowires and biocompatible rubber can be formed by applying a mixture solution with the silver nanowires and the biocompatible rubber onto the PDMS mold, scraping it to fill the inside of the intaglio structure, and drying the solution. The resistance and modulus of the mesh electrode can be adjusted according to the ratio of the mixture solution of the silver nanowires and the biocompatible rubber. If the ratio of the silver nanowires increases, the resistance decreases and the modulus increases. The remaining intaglio structure is filled by applying a second biocompatible rubber solution on the electrode, scraping and drying the solution. If the number of time performing this process, the rubber layer becomes thick.

In the manufacturing method of a mesh electrode according to the present invention, a length of the silver nanowires may range from about 1 μm to about 100 μm, and a diameter of the silver nanowires may range from about 10 nm to about 200 nm. In addition, the silver nanowires may be ligand-exchanged silver nanowires.

In the manufacturing method of a mesh electrode according to the present invention, the first biocompatible rubber may be selected from a group consisting of SBS rubber, TPU, NBR, Hydrogel, PDMS, PUA, PVA, Ecoflex®, PI, PMMA, PVDF. In addition, a thickness of the first biocompatible rubber layer may range from about 1 μm to about 500 μm.

In the manufacturing method of a mesh electrode according to the present invention, the second biocompatible rubber may be selected from a group consisting of SBS rubber, TPU, NBR, Hydrogel, PDMS, PUA, PVA, Ecoflex®, PI, PMMA, PVDF. In addition, a thickness of the second biocompatible rubber layer may range from about 1 μm to about 500 μm.

Advantageous Effects

Most of prior cardiac resynchronization therapy is to connect a catheter to an inside of a heart through vein. The catheter with a small electrode stimulates heart tissue partially, but, since it is difficult to fix the catheter, a large amount is lost when reading signals or giving a stimulus. In addition, since the catheter is located inside the heart through blood vessel, it may influence on the flow of blood. On the other hand, the mesh electrode of the present invention has a low elastic modulus so that it can encircle the heart surface three-dimensionally gently to be fixed. Therefore, it is possible to obtain signals or give a stimulus without any hindrance in movement. In addition, since the area of the electrode is wide, the contact area with the heart is widened to reduce the impedance between electrode and heart. As a result, electrical signals from the heart can be read clearly, and when giving a stimulus, it is possible to stimulate the heart with low threshold value due to the low impedance. Since the mesh electrode is located at the outside wall of the heart, it shares a load according to heartbeats to reduce internal myocardial wall stress.

BEST MODE

Hereinafter, a detailed description will be given of the present invention with reference to the following embodiments. The purposes, features, and advantages of the present invention will be easily understood through the following embodiments. The present invention is not limited to such embodiments, but may be modified in other forms. The embodiments to be described below are nothing but the ones provided to bring the disclosure of the present invention to perfection and assist those skilled in the art to completely understand the present invention. Therefore, the following embodiments are not to be construed as limiting the present invention.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

It will be understood that when an element is referred to as being "on" another element, it can be directly on the other element or intervening elements may be present therebetween. In contrast, when an element is referred to as being "directly on" another element, there are no intervening elements present.

EXAMPLE 1

Large-Scale Synthesis and Ligand Exchange Reaction of AgNW

To synthesize AgNW, a modified $CuCl_2$-mediated polyol process was used (Korte, K., Skrabalak, S. & Xia, Y. Rapid synthesis of silver nanowires through a CuCl- or CuCl2-mediated polyol process. *J. Mater. Chem.* 18, 437-441 (2008)). Eight hundred microliters of 4 mM copper chloride solution ($CuCl_2 \cdot 2H_2O$, 99%; Strem Chemicals Inc., USA) was added to 130 ml of 0.034 M PVP (average molecular weight, 55,000; Aldrich, USA) solution in an oil bath (153° C.), and then 30 ml of 0.094 M silver nitrate ($AgNO_3$, >99% purity, Strem Chemicals Inc., USA) in ethylene glycol solution was injected into the reaction mixture. The synthesis reaction lasted for 1 hour. Next, 0.3 g of synthesized AgNW was dispersed in 6 ml of dimethylformamide (DMF), and 6 ml of 0.1 M NOBF$_4$ was added to the AgNW solution. After 5 min of gentle shaking, hexylamine in hexane (HAm) was added to the reaction solution. The synthesized LE-AgNW solution was diluted with ethanol and centrifuged, and was re-dispersed in toluene.

EXAMPLE 2

Fabrication of the Mesh Electrode

Figure 1A:
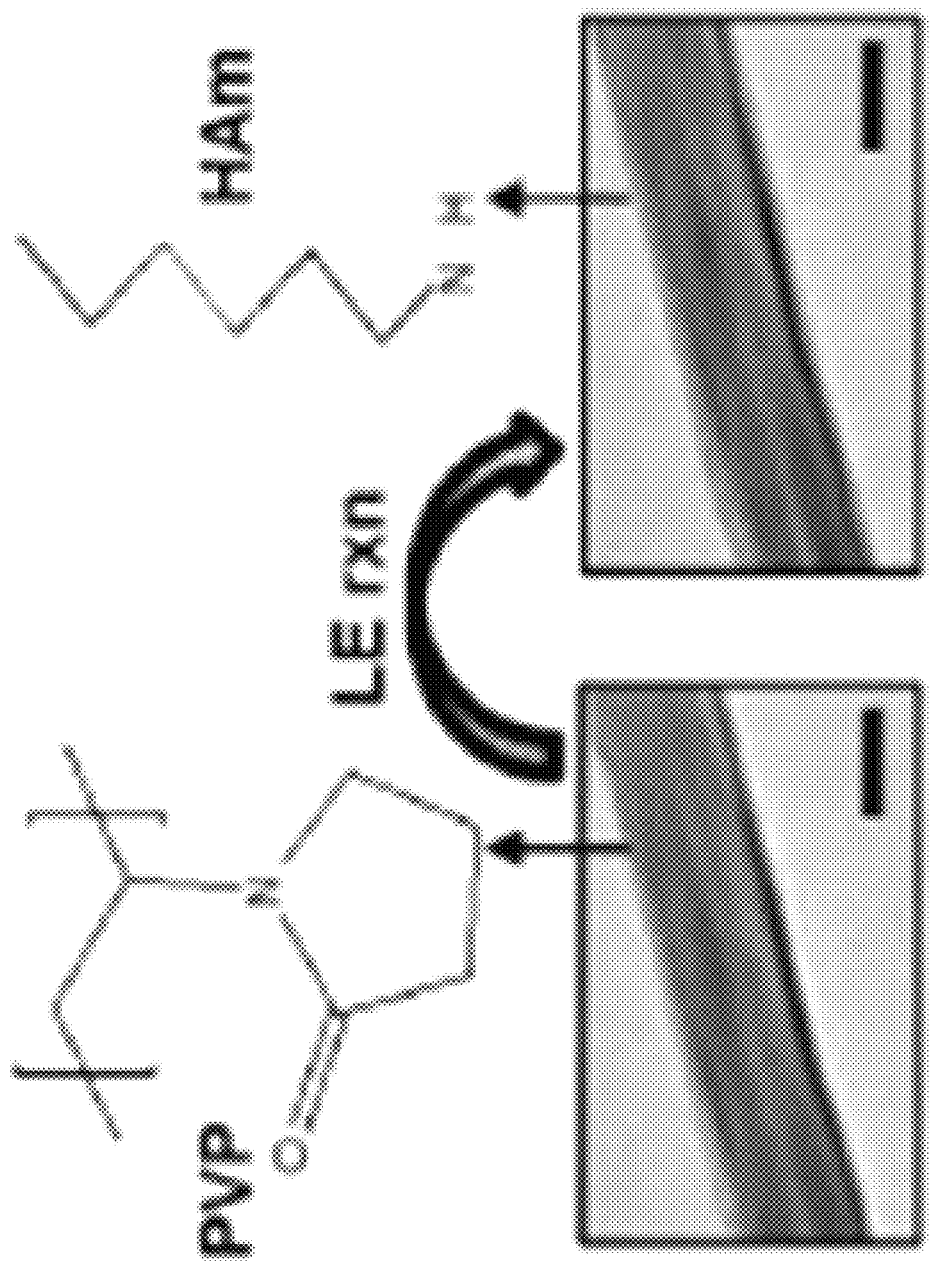
FIG. 1a is a schematic view of the exchange reaction for the ligand of nanowires (AgNW) (scale bar: 50 nm)
Figure 1B:
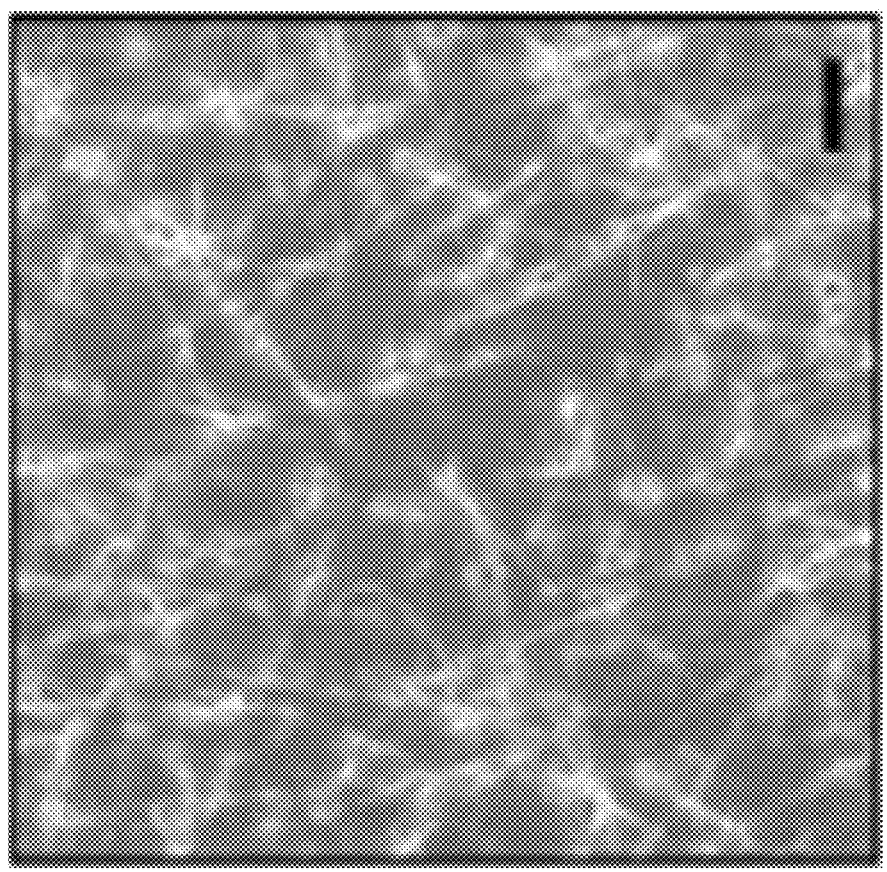
FIG. 1b is a scanning electron microscopy image of a film consisting of ligand-exchanged AgNw/styrene-butadiene-styrene (SBS) (scale bar: 50 μm)
Figure 1C:
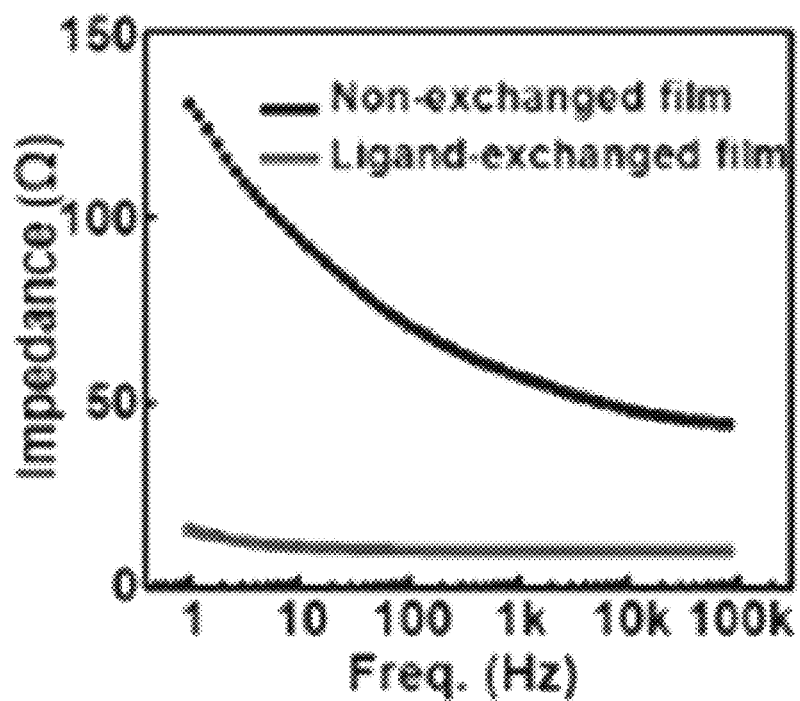
FIG. 1c shows impedance of initial and ligand-exchanged film as a function of frequency of alternating current.
Figure 1D:
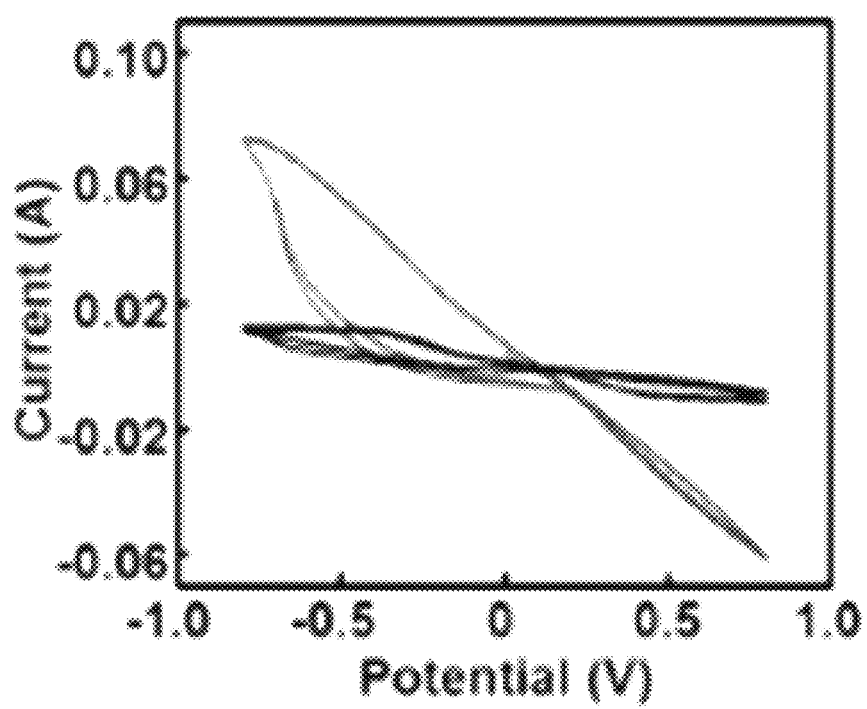
FIG. 1d shows cyclic voltammetry analysis result of initial and ligand-exchanged film.
Figure 1E:
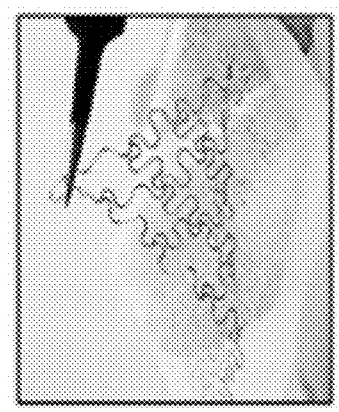
FIG. 1e shows a mold process of an elastic electrode using polydimethylsiloxane.
Figure 1E:
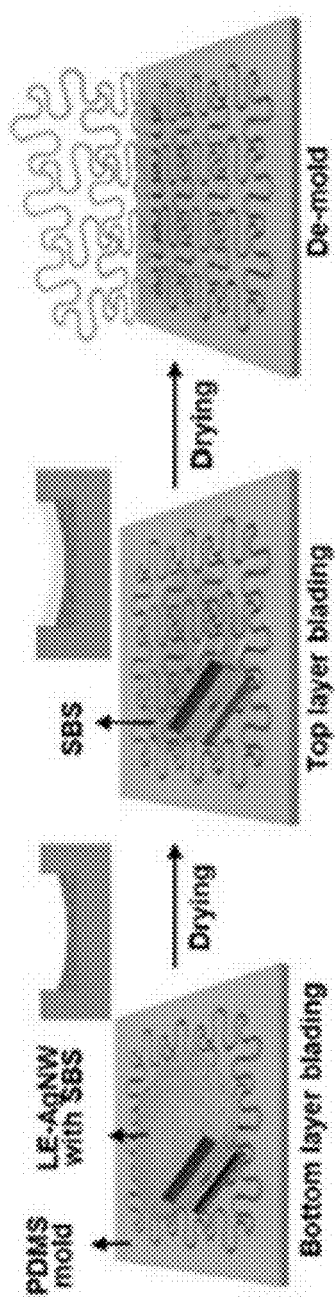

LE-AgNW/SBS (Kumho KTR-101, Kumho Petrochemical, Republic of Korea) ink solution was poured on the serpentine-shaped PDMS mold. The molded solution was dried slowly at 45° C. (FIG. 1e). After forming a conductive elastic polymer of the LE-AgNW/SBS in bottom of PDMS mold, additional SBS solution was poured, severed and dried at the same temperature to encapsulate the LE-AgNW/SBS. The LE-AgNW/SBS ink was applied selectively on the conductive electrode portion to fabricate the epicardial mesh electrodes that are applied to the heart.

EXAMPLE 3

Experimental MI Animal Model

All animal experiments were approved by the Committee for Care and Use of Laboratory Animals, Yonsei University College of Medicine, and performed in accordance with the Guidelines and Regulations for Animal Care. MI (Myocardial infarction) was produced in male Sprague-Dawley rats (320 to 430 g) by a permanent LAD ligation. Briefly, after anesthesia with ketamine (10 mg/kg) and xylazine (5 mg/kg), the hearts were exteriorized by opening the chest with sternotomy. Rats that expired during the procedure were excluded from mortality calculation. Eight weeks after the permanent LAD ligation, rats were intubated and placed on a rodent ventilator (Hugo Sachs Elektronik-Harvard Apparatus, March-Hugstetten, Germany) under zoletil (20 mg/kg) and xylazine (5 mg/kg) anesthesia. Midsternotomy was then performed to expose the hearts, and the epicardial mesh was implanted.

EXAMPLE 4

Stress-Strain Measurements

Stress-strain curves of LE-Ag/SBS film encapsulated in SBS (approximately 10 mm wide and 30-35 mm long), hyperserpentine mesh and epicardial mesh were recorded using a tensile mechanical testing system (ESM301, Mark-10, USA). Stress-strain curves of the epicardial tissue specimens were measured using an Instron-5543 electromechanical system (Instron, USA) controlled by the Bluehill software (Ver. 3). Sprague-Dawley rats (320 g) were sacrificed according to the relevant guidelines and regulations for animal care, and the hearts were excised and stored in ice-cold Hanks' balanced salt solution (HBSS). The epicardial sheets of the left ventricular (LV) wall were dissected and trimmed into circumferentially oriented rectangular specimens (approximately 7 mm wide, 10 mm long and 2 mm thick). Specimens were strained at a rate of 10 mm/min until failure.

Figure 2:
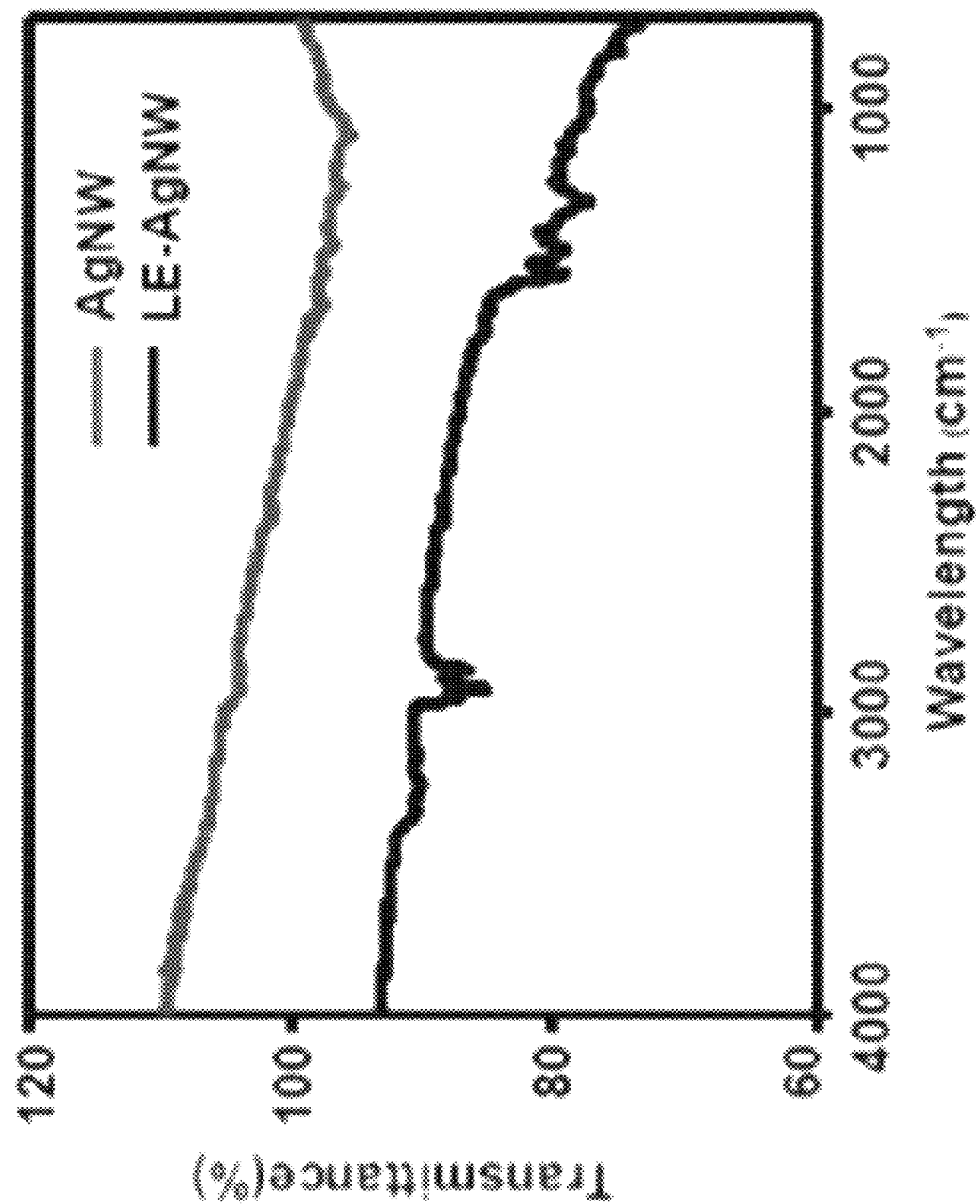
FIG. 2 is Fourier transformed infrared transmittance spectra of AgNW and LE-AgNW (Black and red lines represent peak absorption spectra of AgNW and LE-AgNW, respectively).

Epicardial tissue is elastic and conductive. Silver nanowire (AgNW) networks, one of conductive materials, have a possibility of maintaining conductivity under repeatedly applied strains while encircling the moving heart, due to their high conductivity and mechanical deformability. Styrene-butadiene-styrene (SBS), a biocompatible thermoplastic polymer, has high elasticity and reshaping capability because of its physically cross-linked structure. We, inventors attempted a uniform mixture of AgNW in SBS rubber to provide elasticity and stable electrical conductivity. To achieve this, ligand exchange of AgNW (LE-AgNW) is necessary for homogeneous dispersion in the organic-phase SBS solution. Polyvinylpyrrolidone (PVP) ligand of AgNW was partially exchanged to hexylamine (HAm) using NOBF$_4$ (FIGS. 1a and 1b), and thus a phase transfer of the water-dispersed AgNW to the organic phase occurred. The increased peak intensity of N—H bond stretching in the Fourier transform infrared spectroscopy spectra confirmed successful ligand exchange reaction (FIG. 2). Compared to AgNW/SBS film without ligand exchange, LE-AgNW/SBS film exhibited consistently lower impedance for different frequency inputs (FIG. 1c) and larger charge injection for different voltage inputs (FIG. 1d). This indicates stable electrical conduction of the elastic polymer. The conductivity of LE-AgNW/SBS film also depends on the mixing ratio of LE-AgNW to SBS. If the proportion of LE-AgNW increases, electrical conductivity improves, but mechanical elasticity is deteriorated. A film with LE-AgNW/SBS ratio of 65:35 conferred the optimal conductivity of 25,000 S/cm under which the heart can act synchronously by the quick conduction through the mesh. However, mechanical properties of the mesh such as elasticity are still inferior to those of epicardial tissue.

Figure 1F:
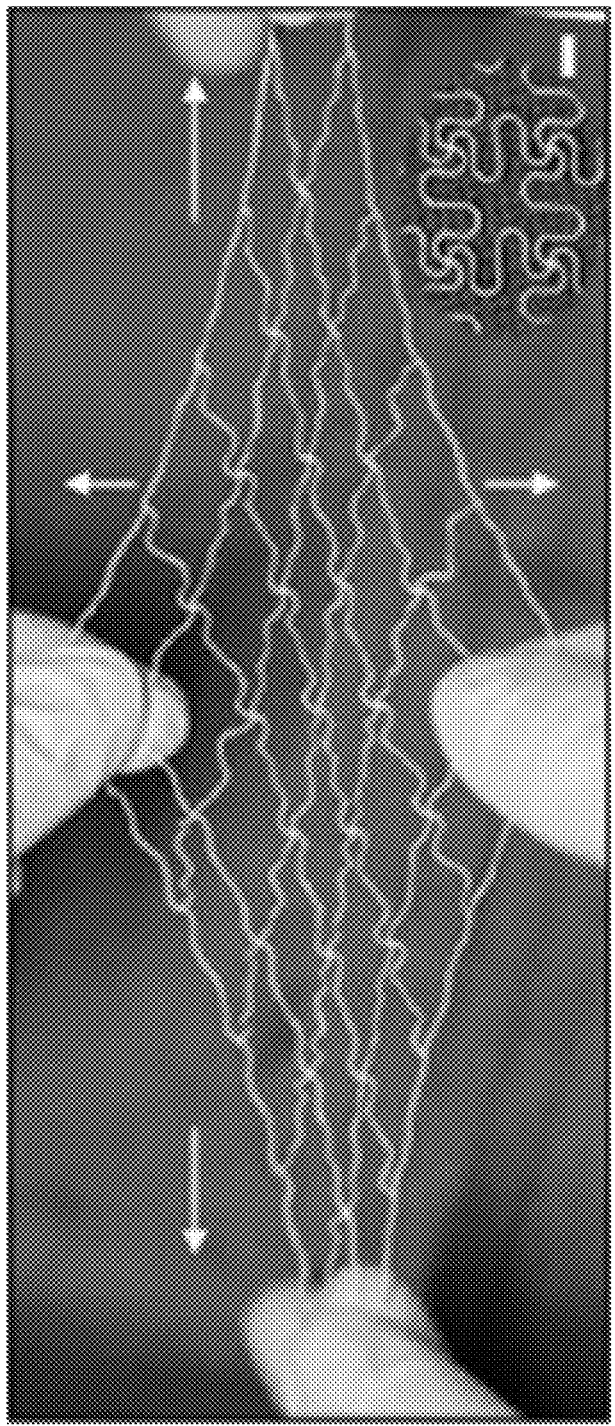
FIG. 1f is an image for quadrate serpentine mesh extended in horizontal and vertical directions by 150% and 10% (the inset shows the serpentine mesh before being extended) (scale bar: 50 mm)
Figure 1G:
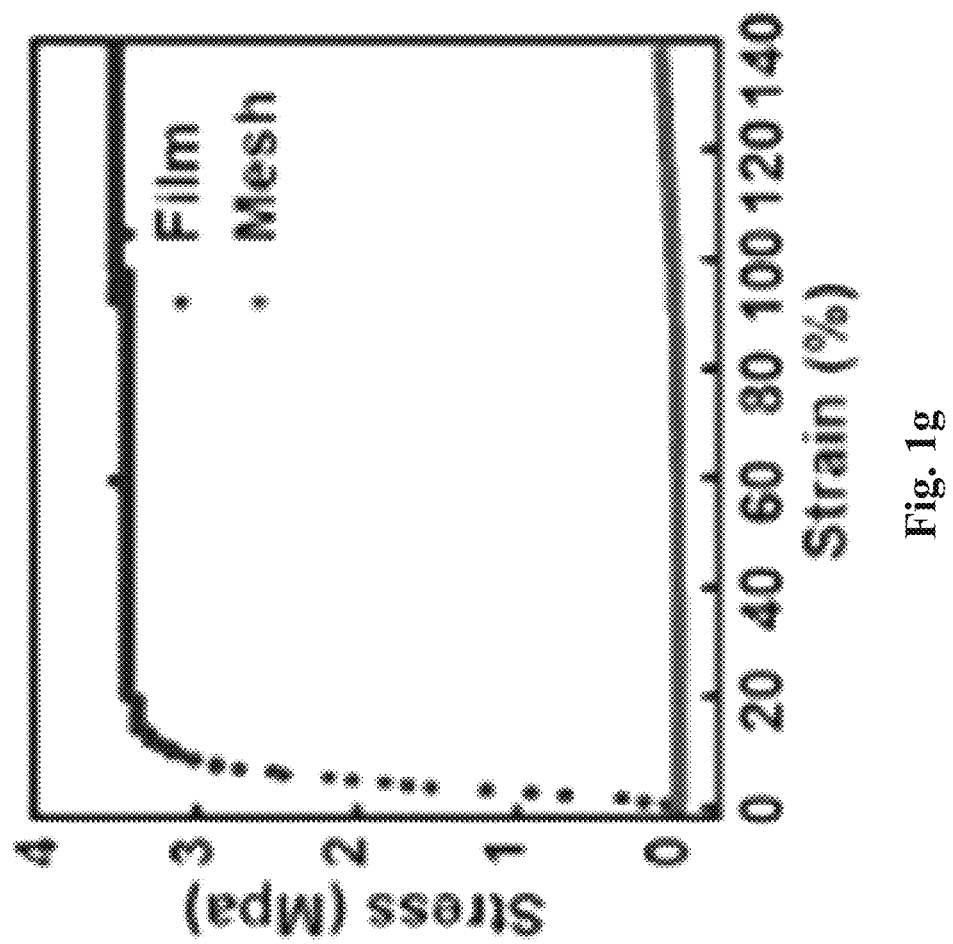
FIG. 1g is a stress-strain curve of quadrate serpentine mesh.
Figure 1H:
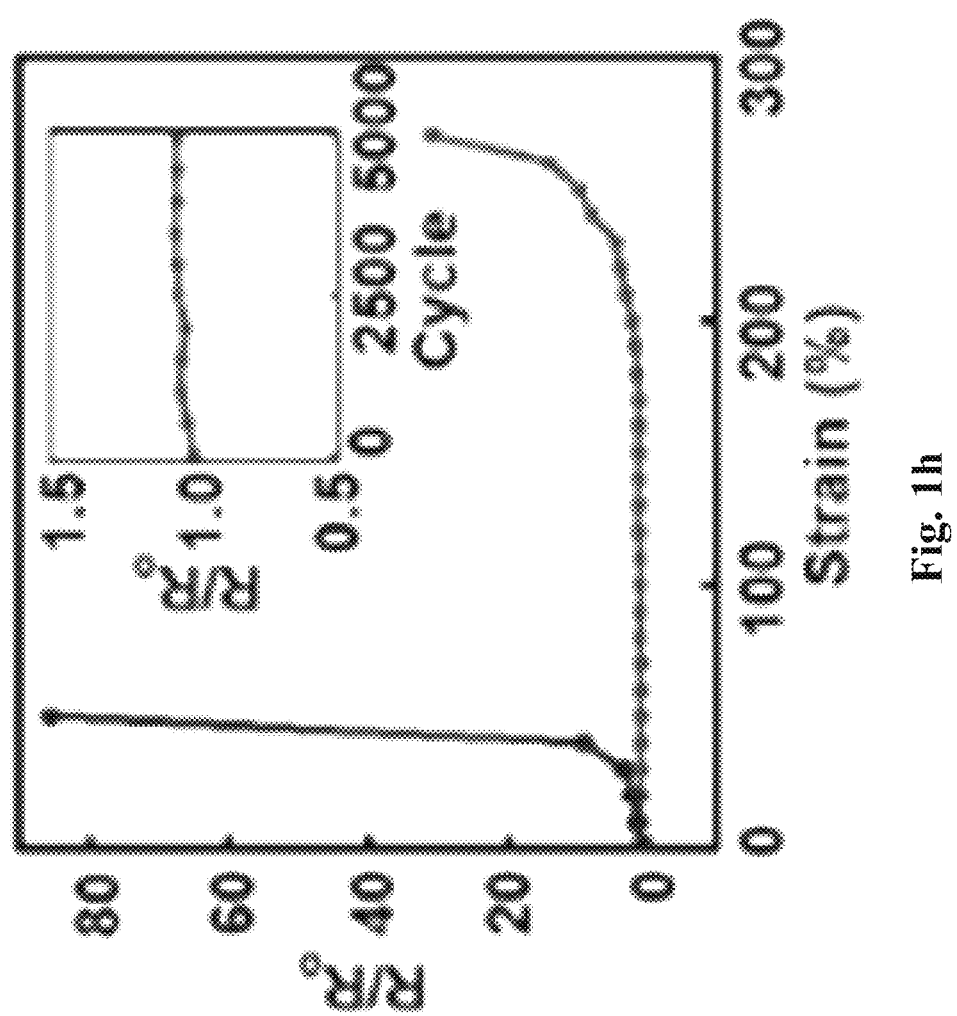
FIG. 1h shows the relative resistance change of film and quadrate serpentine mesh under increasing strain.
Figure 3A:
FIG. 3a is stacked CT (computed tomography) images (left panel), a transaxial CT image (mid panel) and 3D heart reconstruction image (right panel)
Figure 3B:
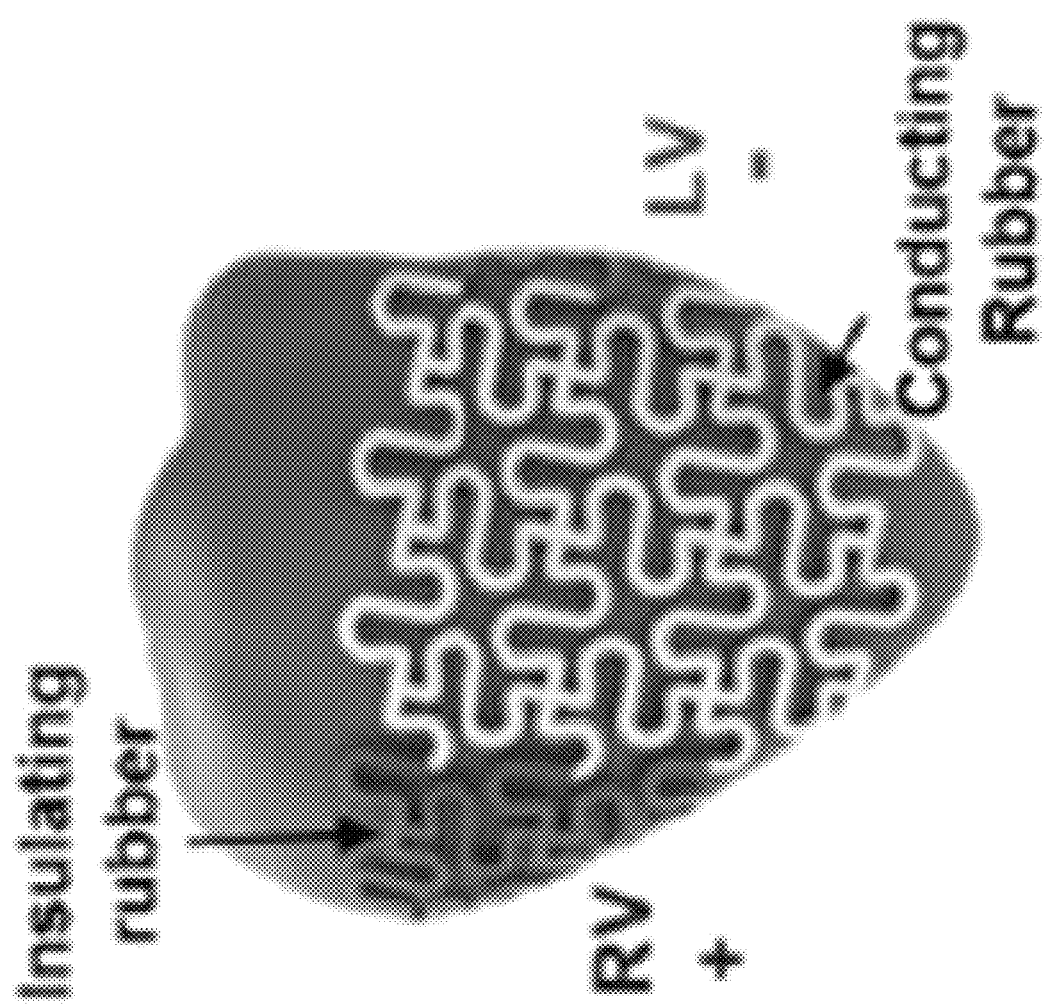
FIG. 3b shows adjustments (RV, right ventricle; LV, left ventricle) of size and location of epicardial mesh electrode using 3D heart simulation model.
Figure 3C:
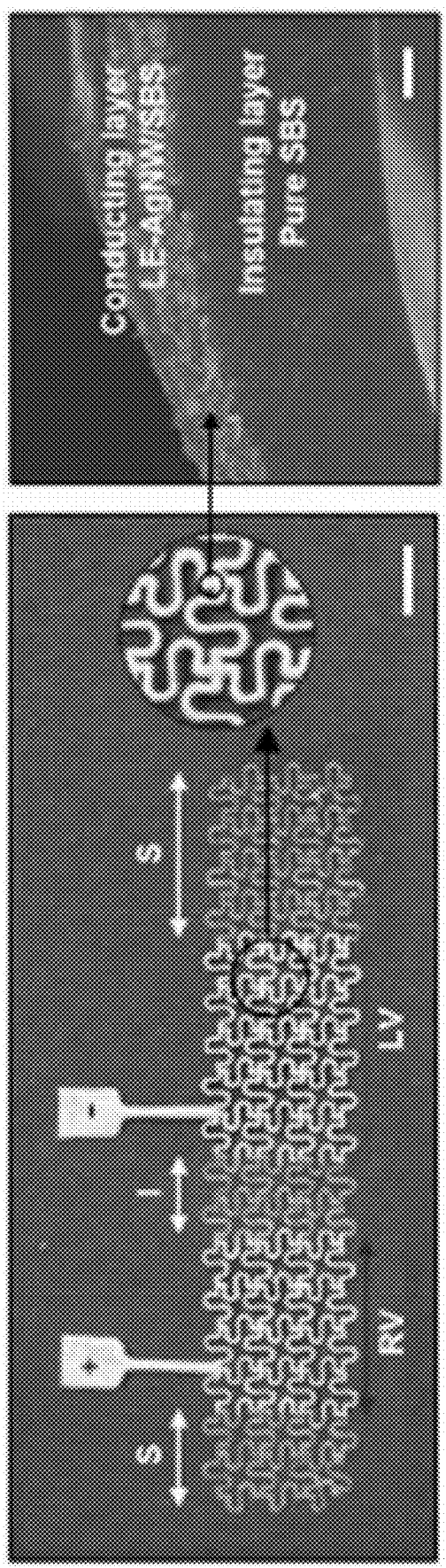
FIG. 3c is a plan view of the epicardial mesh composed of an insulated part (I) connecting negative electrode and positive electrode, and supporting parts (S) (cross section of the electrode portion represents conductive and insulation layer (right panel)) (scale bar: 5 mm (left), 10 μm (right))
Figure 3D:
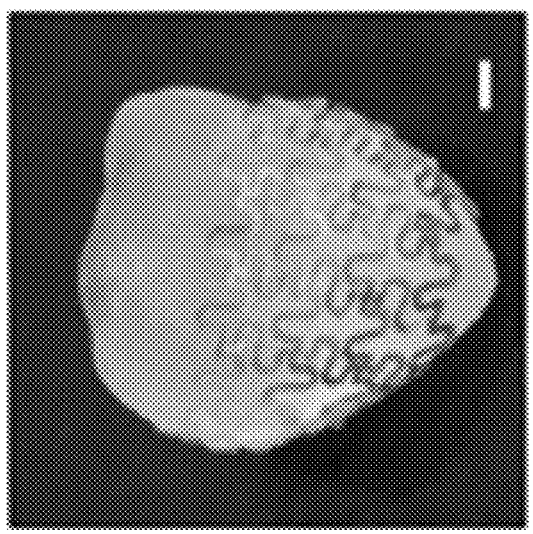
FIG. 3d is a real photograph of the mesh electrode encircling the 3D printed heart model (scale bar: 1 mm).

Encircling the heart with a stiff film decreases diastolic compliance and increases LVEDP (ventricular end-diastolic pressure), thereby aggravates heart failure symptoms. Therefore, we, inventors aimed to create a device with mechanical properties similar to those of the myocardium to conform to and integrate with the epicardial surface. To improve the mechanical elasticity, a serpentine mesh of the LE-AgNW/SBS was fabricated using a polydimethylsiloxane (PDMS) mold (FIGS. 1e and 3a). We, inventors confirmed that the serpentine mesh of the LE-AgNW/SBS is much superior to the film electrode in terms of mechanical and electrical properties. FIG. 1f shows that the serpentine mesh can be stretched in an oblique direction by 150% in comparison with the original size (See FIG. 3b). When applying an uni-axial strain by 0~140%, Young's modulus of the serpentine mesh (E=stress/strain=213 kPa) is smaller than that of the film type electrode (E=47 MPa) (FIG. 1g). In addition, under the application of strains, the film electrode exhibited a great change in its electrical resistance whereas the serpentine mesh exhibited minimal change in its electrical resistance (FIG. 1h). These mechanical—electrical properties were maintained over repetitive stretching cycles (FIG. 1h, inset), and thus the serpentine mesh more suitable for clinical applications was fabricated.

Figure 1I:
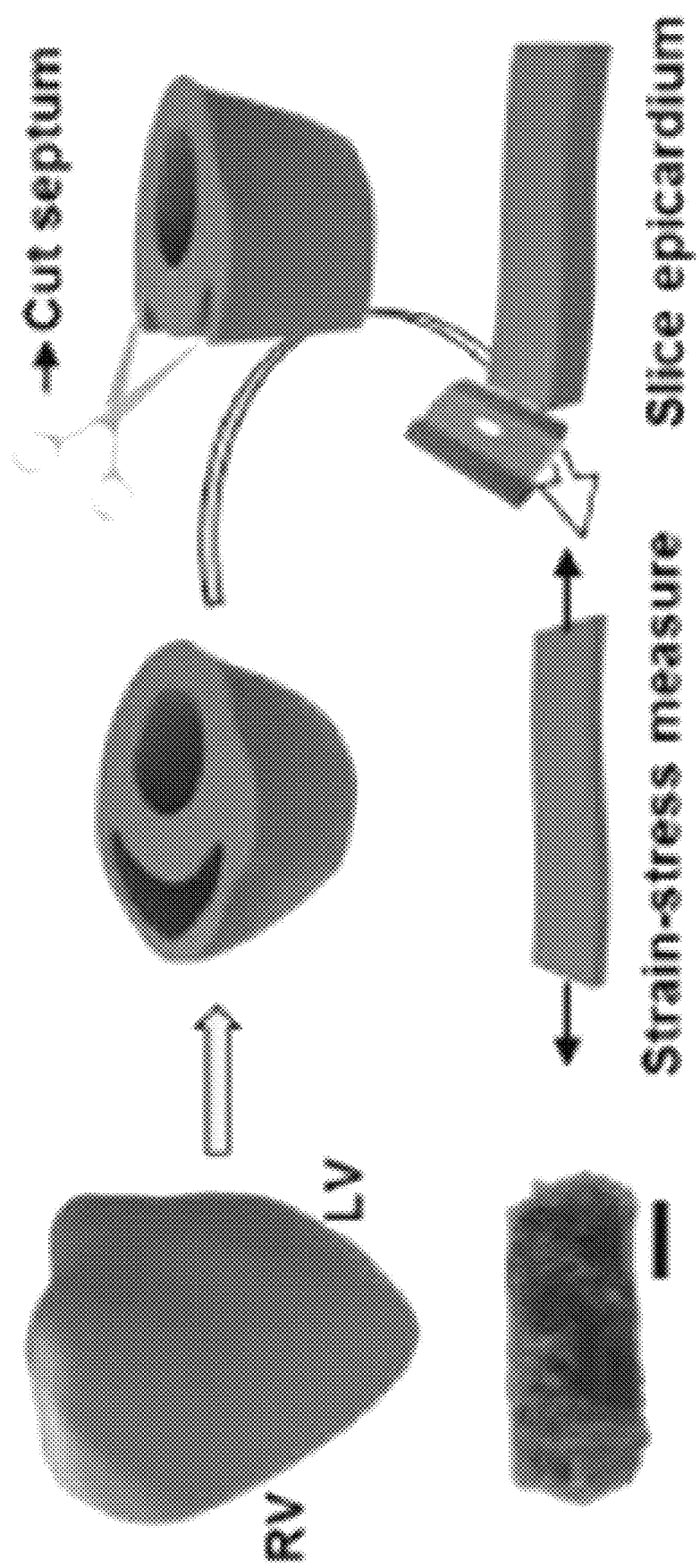
FIG. 1i is a schematic view of experimental process for measuring the elastic modulus of the epicardial tissue sheet (scale bar: 50 mm), FIG. 1j a strain-stress curve of the epicardial sheet and serpentine mesh (RV, right ventricle; LV, left ventricle)
Figure 1J:
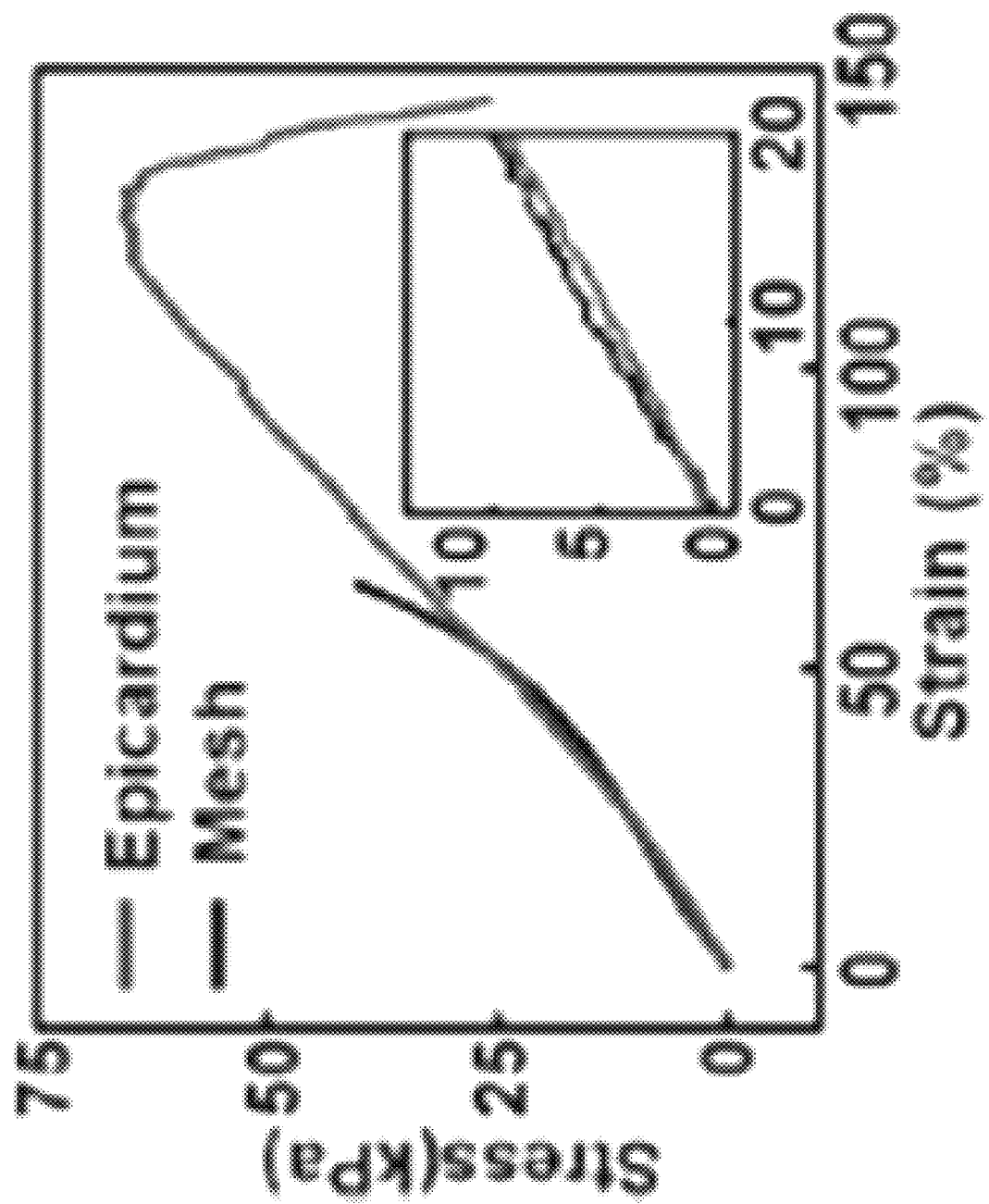
FIG. 1k is circumferential strain of the outer layer of the heart (left panel), and movements of the mid-ventricular epicardial layer measured by two-dimensional echocardiography (right panel) (red circle, end diastole; blue circle, end systole) in control heart (n=2) and 8-week post-MI rat heart (n=2) (scale bar: 1 cm).
Figure 1K:
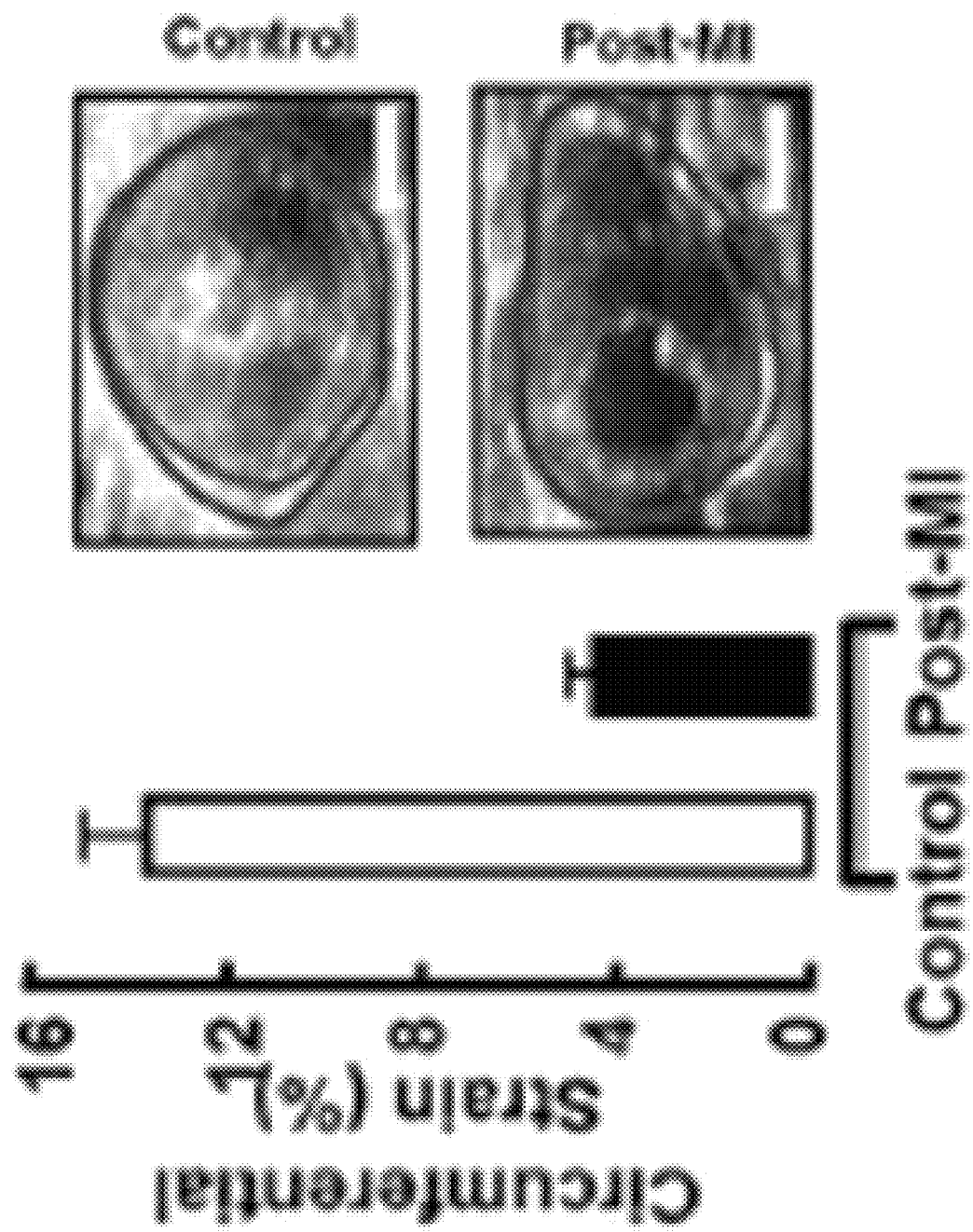

In order to check whether the mechanical properties of the serpentine mesh are similar to those of the epicardium, as shown in FIGS. 1i and 1j, we, inventors measured the Young's modulus of 2-mm-thick epicardial tissue sheets resected from rat (n=2) hearts. The average strain of the outer layer of the heart measured by echocardiography was 14.1% in control rats (n=4) and 4.6% in 8-week post-myocardial infarction rats (n=3) (FIG. 1k). The important point is that the elastic modulus of the serpentine mesh (E=44.3 kPa) was almost the same as that of the epicardial tissue (E=40 kPa) within a range of the circumferential strain observed in the outer layer of the heart (FIG. 1j, inset).

EXAMPLE 5

Cardiac Computed Tomography (CT)

CT scans for 3D printing were performed using a second-generation dual-source CT (SOMATOM Definition Flash, Siemens Medical Solutions, Forchheim, Germany). First, a non-enhanced CT image was obtained to confirm the scan range and the location of the aortic arch for bolus tracking. The scan range is from the lung apex to the diaphragm. Next, contrast CT was performed with 2 mL/kg of contrast media (Iopamiro 370, Bracco, Italy), which was injected into a tail vein. The initial delay was defined by bolus tracking in the aortic arch, and the scan was automatically initiated 2 seconds after reaching the threshold of 400 HU. Scanning was performed using the following parameters: high pitch spiral acquisition, 80 kVp, 50 mAs, 64×0.6 mm slice collimation, and 330 ms gantry rotation time. The mean scanning time was 0.90 s. CT images were reconstructed using a slice thickness of 0.75 mm, increment interval of 0.5 mm, and medium-smooth convolution kernel B36f. The field of view was adjusted according to the thorax size.

EXAMPLE 6

Computer Simulations

High-resolution micro-CT images were segmented, and a 3-dimensional finite element mesh for biventricular geometry below the valve plane was obtained (Young, P. G. et al. An efficient approach to converting three-dimensional image data into highly accurate computational models. *Philos. Trans. A. Math. Phys. Eng. Sci.* 366, 3155-73 (2008)). The finite element mesh consisted of 48,832 quadratic tetrahedrons for the myocardium and 16,296 quadratic triangular shell elements for the sock. Because the myocardium was made of incompressible hyperelastic materials, large deformation, large strain, hybrid formulation was implemented. The neo-Hookean model was used in order to approximate the myocardiac behavior (Dokos, S., LeGrice, I. J., Smaill, B. H., Kar, J. & Young, A. A. A Triaxial-Measurement Shear-Test Device for Soft Biological Tissues. *J. Biomech. Eng.* 122, 471-478 (2000)). The wrap material behavior was described using different linear elastic properties for each case (500 Pa for the mesh wrap, and 4,000 MPa for the film wrap). Out-of-plane motion of nodes on the top surface was constrained. A pressure of 100 mmHg was applied on the LV. RV pressure was disregarded since it does not appreciably affect the LV pressure-volume relation because of the thicker LV wall and smaller RV pressure. There was no relative sliding motion between the sock and the underlying myocardium. The total thickness of the shell was set to 88 µm based on the measurement of epicardial mesh samples by scanning electron microscopy. To assess the effect of the epicardial mesh on the ventricular chambers, EDPVR (end-diastolic pressure volume relation) was calculated.

In order to achieve global electrical resynchronization, the epicardial mesh was redesigned as shown in FIG. 3. The device was composed of two wide serpentine mesh electrodes, an insulating part between the cathode and anode, and supporting parts to assist wrapping the heart along with a wiring pad (+ and −) (FIG. 3c). In order to prevent unintended electrical stimulus, the outer part of the epicardial mesh was coated with an SBS insulating layer (FIG. 3c, right panel). Stacked cardiac CT images for a rat heart was used to make an anatomically personalized design for the epicardial mesh electrode (FIG. 3a). After adjusting the size of the epicardial mesh and the location of the electrode on three-dimensionally reconstructed image (FIG. 3b), the final design and size for the fabricated mesh on 3D printing model heart was improved (FIG. 3d).

Figure 4A:
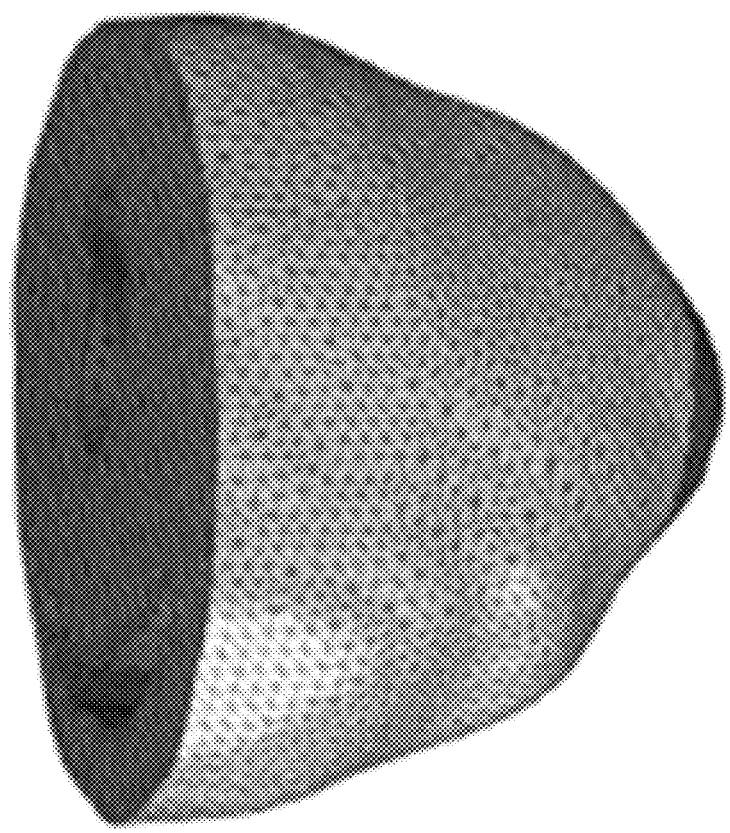
FIG. 4a shows biventricular finite element (FE) mesh model (left panel) (gray layer represents wrapped device (right panel))
Figure 4A:
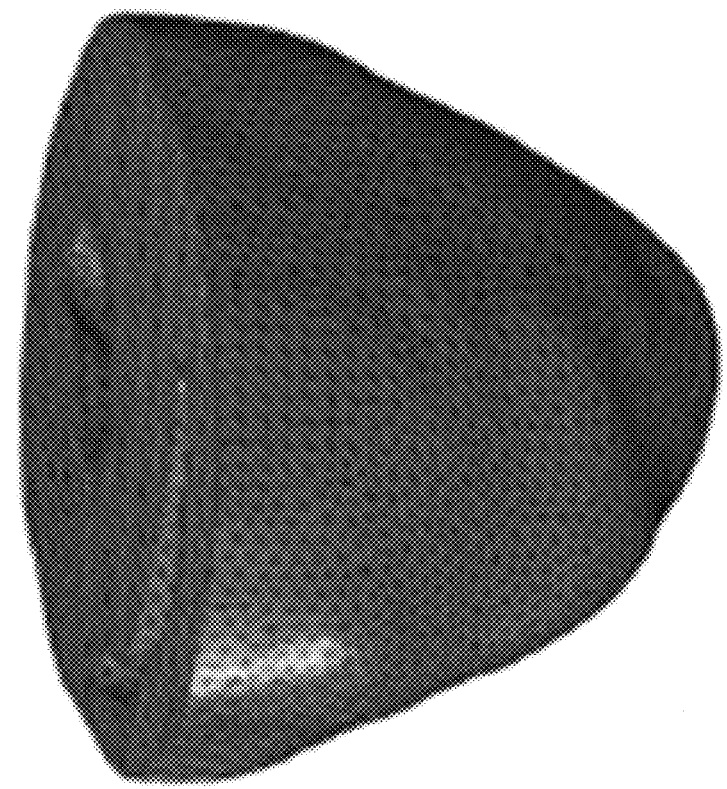
Figure 4B:
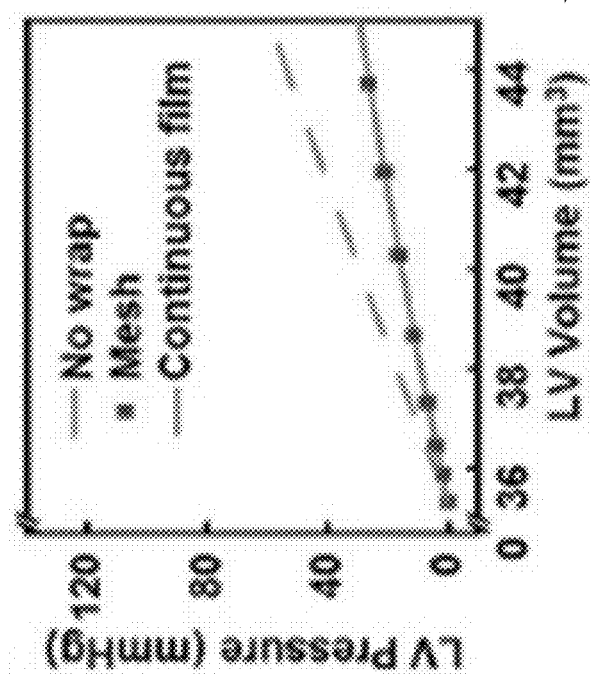
FIG. 4b shows effects of the mesh wrap and the film wrap on the left ventricle end-diastolic pressure-volume (EDPVR)
Figure 4C:
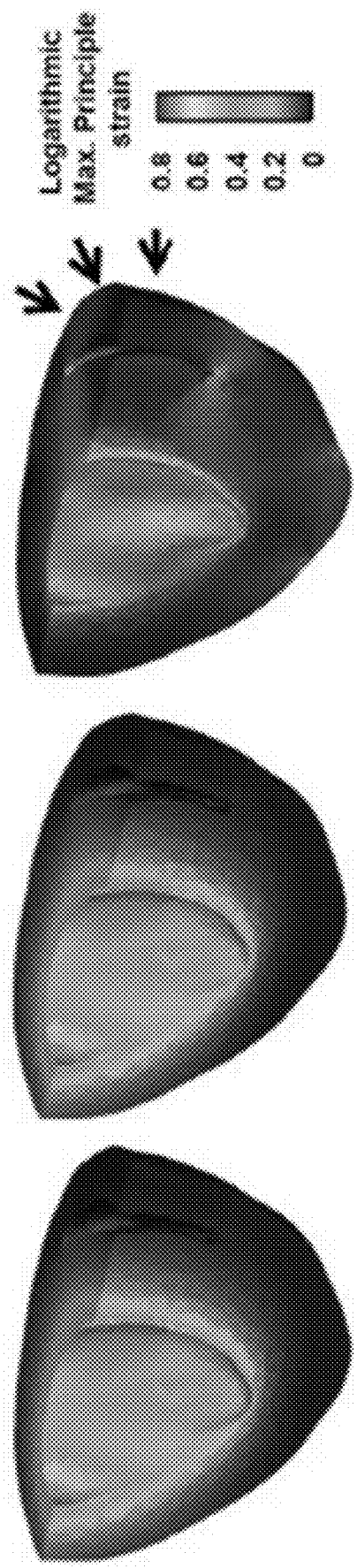
FIG. 4c is logarithmic maximum principal strain distribution without any wrap, with the mesh wrap, and with the continuous film wrap.

We, inventors attempted to simulate the mechanical effects of the epicardial mesh on rat heart diastolic function. Using a biventricular finite element model (FIG. 4a) based on high-resolution CT images for rat hearts ex vivo, diastolic expansions of three cases were compared: (i) without any wrap on the heart, (ii) with the wrap using epicardial mesh (E=50 kPa), and (iii) with continuous thin film (E=47 MPa in LE-Ag/SBS film) on the heart. FIG. 4b shows effects of the mesh or the film wrap on the end-diastolic pressure-volume relationship (EDPVR). When compared to the control, the continuous film wrap moved the EDPVR curve to the left (small adaption), whereas the epicardial mesh wrap made of the same materials did not show any appreciable effect. FIG. 4c shows the comparison of logarithmic maximum principal strain. In particular, the application of the film to hearts caused diastolic collapse in the RV (FIG. 4c) implying a significant risk of hemdynamic instability. In contrast, the epicardial mesh wrap did not affect the shape or curvature of ventricular chambers during the cardiac cycle. To sum up, the computer simulation results show that the mesh is superior to the film in terms of hemodynamic stability.

EXAMPLE 7

Surface Electrocardiography and Electrophysiological Studies

Surface six-lead ECG (lead I is shown in figures) was continuously recorded along with all intracardiac electrograms and stored in the amplifier/recorder system (Pruka CardioLab IT System, GE Healthcare, Milwaukee, Wis.). The sampling rate was 4 kHz. R-R intervals, QRS durations, and QT intervals were measured as described previously (Berul, C. I., Aronovitz, M. J., Wang, P. J. & Mendelsohn, M. E. In vivo cardiac electrophysiology studies in the mouse. *Circulation* 94, 2641-2648 (1996), Mitchell, G. F., Jeron, A. & Koren, G. Measurement of heart rate and Q-T interval in the conscious mouse. *Am. J. Physiol.* 274, H747-H751 (1998)). For the QTc interval measurement, Bazett's formula was used (Bazett, H. C. An analysis of the time-relations of electrocardiograms. *Ann. Noninvasive Electrocardiol.* 2, 177-194 (1997)). All parameters were measured twice by a cardiologist and a blinded investigator. The intra-observer variability was <10% for the cardiologists and electrophysiologists. Intracardiac electrograms were obtained from an epicardial mesh electrode and a 4 F bipolar electrode catheter (2-mm interval; St. Jude Medical, St. Paul, Minn.). Stimulation was performed twice at the pacing threshold of rectangular stimulus pulses with duration of 2 ms by a programmable digital stimulator (Bloom DTU 215, Fisher Medical Technologies, Denver, Colo.). Ventricular tachycardia was defined as at least four ventricular beats and identified on the basis of atrioventricular dissociation on the intracardiac electrogram.

EXAMPLE 8

LV Catheterization

LV catheterization was performed for invasive hemodynamics. A Millar Mikro-tip 2 F pressure transducer (model SPR-838, Millar Instruments, Houston, Tex.) was introduced into the LV via the apex. Real-time pressure loops were recorded, and all data were analyzed off-line with the PVAN 3.5 software (Millar) by an independent investigator.

EXAMPLE 9

Echocardiography

An echocardiograph (Vivid i, GE Healthcare) was used with an 11 MHz M12L-RS linear array transducer. The parasternal short axis of the mid-LV was used for the study. Image depth was 2-2.5 cm with 234-340 frames/s acquisition using second harmonic imaging. ECG gating was used.

EXAMPLE 10

Speckle Tracking Radial Strain

Non-Doppler strains were measured using a dedicated software package (EchoPac PC; GE Healthcare) as described previously (Migrino, R. Q. et al. Assessment of segmental myocardial viability using regional 2-dimensional strain echocardiography. *J. Am. Soc. Echocardiogr.* 20, 342-351 (2007)). For each cardiac cycle (defined from the peak of the R wave to the following R wave), the endocardial border was manually traced at end-systole. Adequate tracking was verified in real time and the tracking was corrected by adjusting the region of interest or manually correcting the contour to ensure optimal tracking. The outer border was adjusted to approximate the epicardial contour. The software automatically computed radial strain in 6 segments of the mid-LV throughout the cardiac cycle. End-systole was defined as the time point when the radial strain rate becomes zero after being positive. Data were analyzed off-line by an independent investigator twice. Intra-observer variability was <10%.

EXAMPLE 11

Myocardial Wall Stress

Two-dimensional echocardiogram (Vivid i, GE Healthcare) was recorded simultaneously with pressure in the LV cavity with a Millar catheter. Data for analysis were collected when the pressure waveform was not distorted by the echocardiographic transducer on the heart. Time-resolved numerical values of radial strain and displacement obtained from the echoPAC software were transferred to Matlab (Mathworks, US). Myocardial stress was also processed by Matlab using the method of Chirinos (Chirinos, J. A. et al. Time-varying myocardial stress and systolic pressure-stress relationship: role in myocardial-arterial coupling in hypertension. *Circulation* 119, 2798-2807 (2009)).

EXAMPLE 12

Histological Analysis

Hearts were fixed in 10% formalin solution for 24 hours at 4° C. Paraffin blocks were made, and 2 µm slides were prepared by Masson's trichrome staining.

EXAMPLE 13

Statistical Analysis

Data were expressed as means±SEM for continuous variables and as proportions for categorical variables. For parametric variables, statistical analyses of pairs of groups and samples were conducted with Student's t test and matching sample t test, respectively. A linear mixed model was used to account for repeated measurements in each group. In the linear mixed model, animals were included as random effects and conditions (sinus rhythm, presence or absence of mesh), pacing (420, 320 and 280 ms), and interactions that were treated as fixed effects. Appropriate contrasts were selected to analyze differences between pacing levels and conditions. Differences in end-diastolic pressure, maximum and minimum dP/dt, and tau values between groups at sinus rhythm and each pacing cycle length (420, 320, and 280 ms) were compared. P<0.05 was considered to represent a statistically significant difference. Statistical analysis was performed using the SPSS package for Windows (version 18.0; SPSS Inc., Chicago, Ill., USA).

Figure 5A:
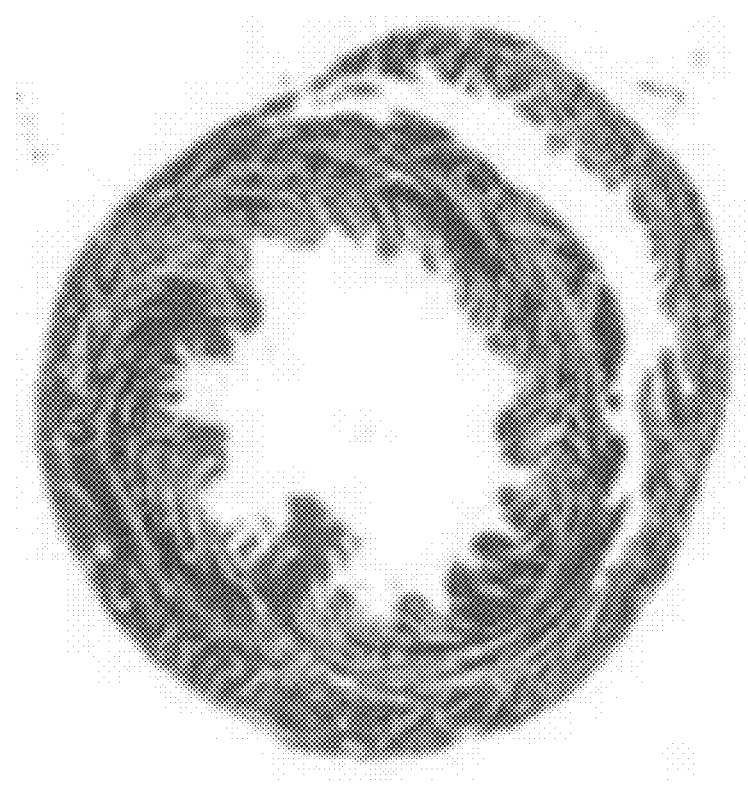
FIG. 5a shows the result of Masson's trichrome staining on a control heart.
Figure 5B:
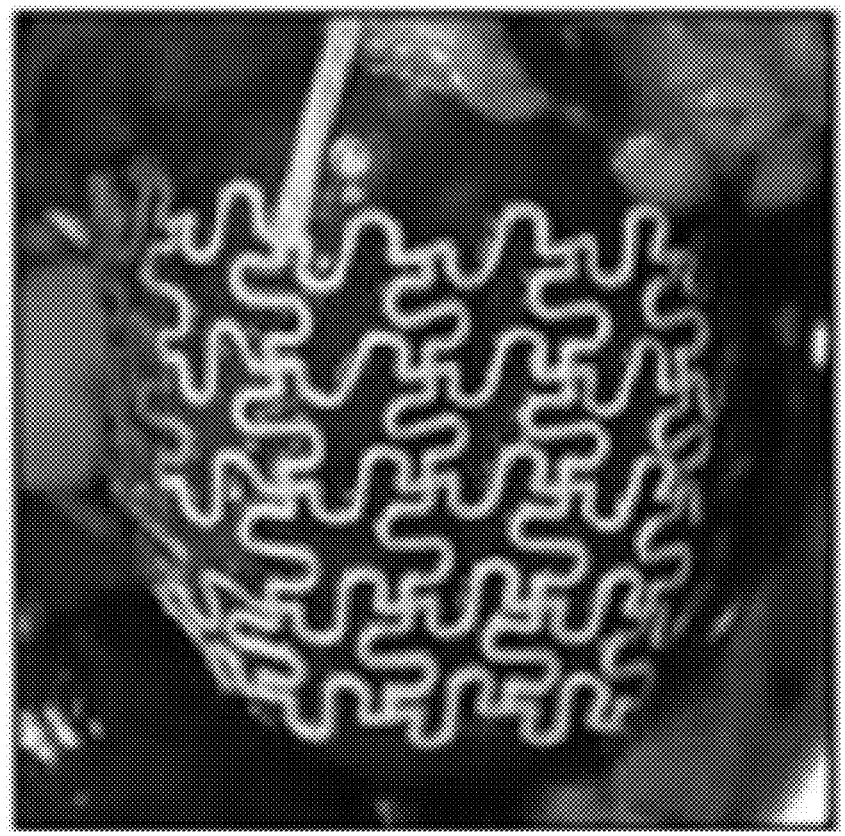
FIG. 5b is the photograph of the epicardial mesh implanted in a control heart, FIG. 5c epicardial electrograms recorded from the epicardial mesh at cycle length of 280 ms during global resynchronization pacing by the epicardial mesh (upper trace, surface lead I electrograms; middle trace, right ventricle apex electrograms; lower trace, epicardial electrograms)
Figure 5C:
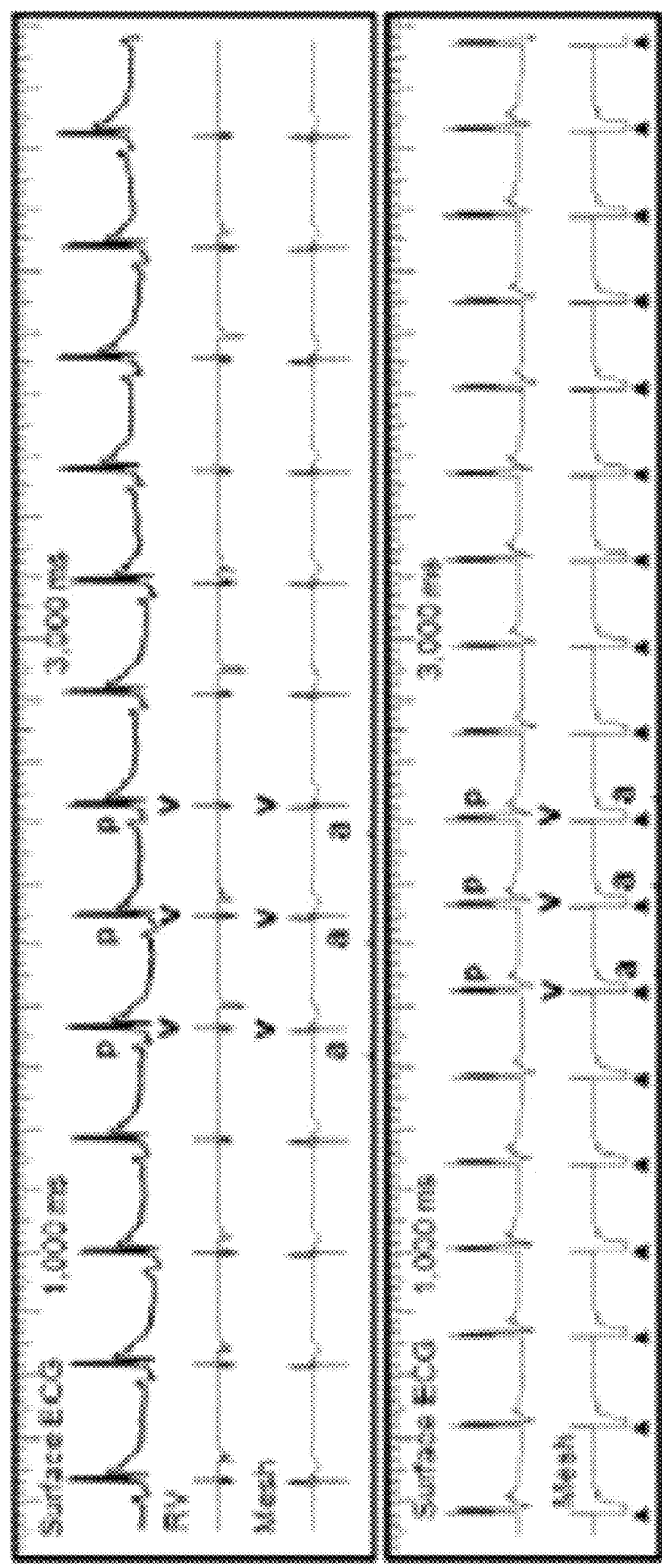
FIG. 5d is surface electrograms (ECG) record (lead 1) in control hearts during global resynchronization pacing and sinus rhythm (SR) using epicardial mesh.
FIG. 5e is 3D phase attractor of phase consistency of electrograms recorded from the epicardial mesh (right panel) and a bipolar electrode (left panel) located at the epicardial surface of RV apex (t is time, d is delay time (1.28 ms). The lower end pattern in right panel graph is more stable in comparison with left panel. EGM, electrogram)
FIG. 5f is the real photograph of post-MI heart 8 weeks after left anterior descending artery (LAD) ligation (arrow represents infarction lesion)
FIG. 5g is transmural scar of Masson's trichrome staining, FIG. 5h the photograph of MI heart where the epicardial mesh was transplanted.
FIG. 5i is surface ECG (upper trace) showing frequent occurrence of wide QRS tachycardia appearing as non-persistent ventricular tachycardia from epicardial mesh record (lower trace)
FIG. 5j shows degeneration 3 seconds after ventricular fibrillation and a successful termination of a biphasic electrical shock of 2 J delivered through the epicardial mesh.
FIG. 5k is surface ECG record (lead 1) from sinus rhythm (SR) and epicardial mesh pacing (MeshP) in 8-week infarction rats.
FIG. 5l shows the effect of global resynchronization therapy to QRS duration in control rats (n=9) and post-infarction (post-MI) rats (n=12) (The epicardial mesh pacing and right ventricle pacing (RVP) were conducted for 8 rats and 7 rats of 9 control rats, respectively. The epicardial mesh pacing was done for 10 rats of 12 post-infarction rats. Statistical evaluation was performed using unpaired t-test. *p<0.05, p<0.01)
FIG. 5m is paired comparison between baseline and epicardial mesh pacing in 8 control rats and 10 post-MI rats (Statistical evaluation was performed using paired t-test. *p<0.005).
Figure 5D:
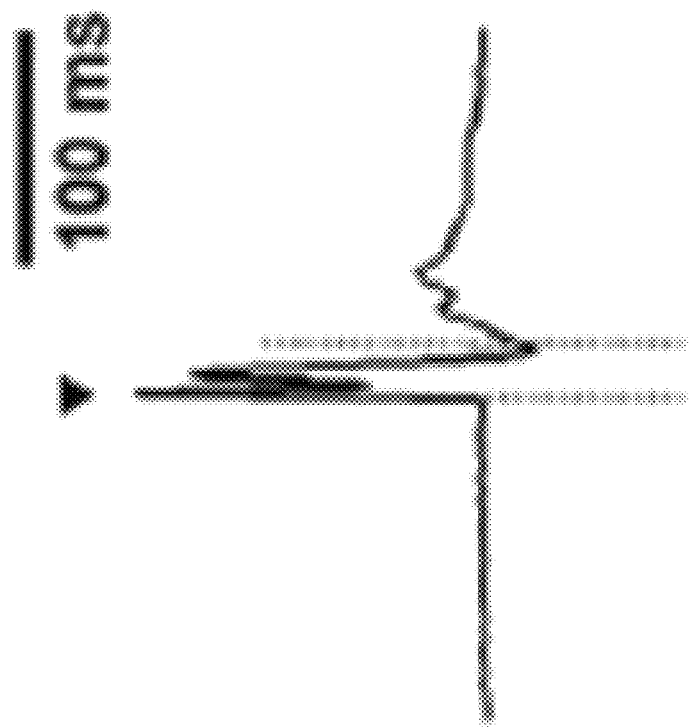
Figure 5D:
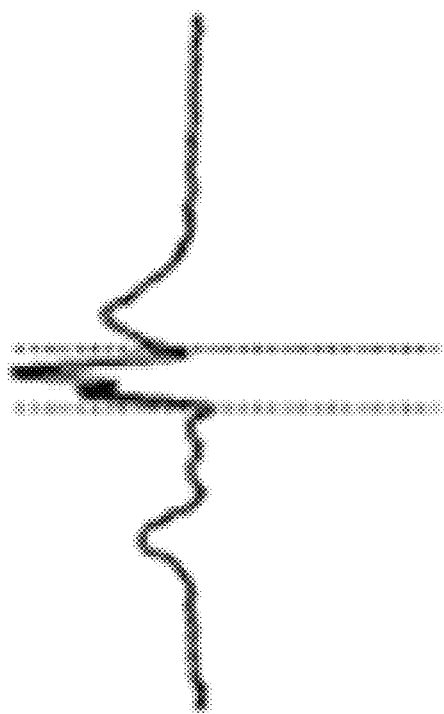
Figure 5E:
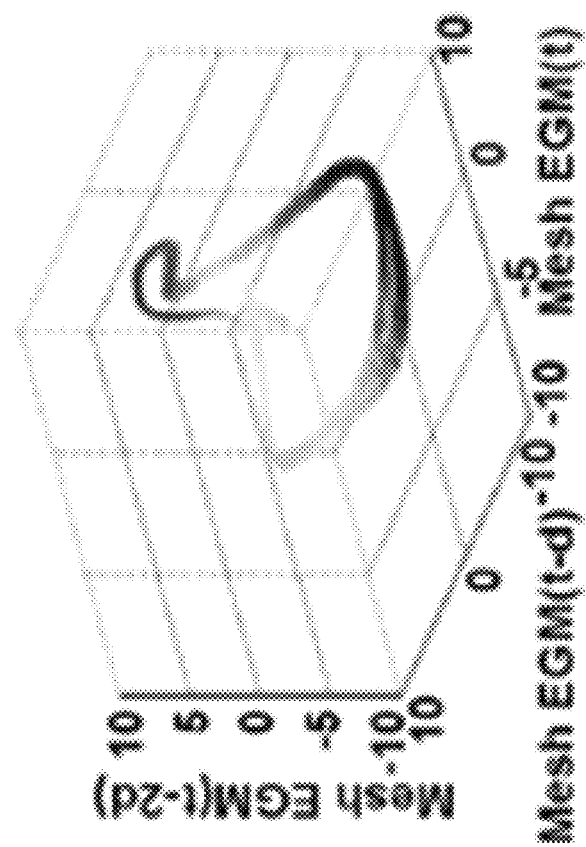
Figure 5E:
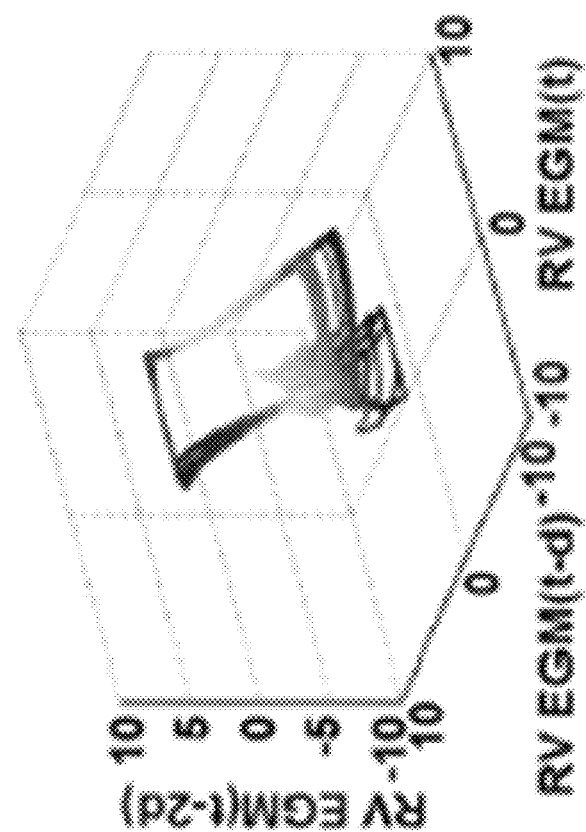

Electrical and mechanical effects of the serpentine epicardial mesh were tested using hearts of control and post-MI rats. First, the electrical sensing and pacing function were measured in the control (n=9; FIGS. 5a and 5b). Baseline surface electrocardiogram (ECG) was recorded after intubation and sternotomy, a custom-fitted epicardial mesh covering the entire surface of both ventricles was implanted in the control (FIG. 5b). The electrical activity of both ventricles was recorded using the bipolar electrode of the epicardial mesh (FIG. 5c). Electrograms recorded from the epicardial mesh exhibited stable ventricle signals without any visible baseline drifts. In contrast, baseline drift was evident in electrograms from the bipolar electrode located at the right ventricle (FIGS. 5c and 5e). After subtracting QRS-T complexes, the baseline drift shown in the electrograms of the epicardial mesh decreased significantly, suggesting that the epicardial mesh was well integrated and assimilated to the epicardial surface of the moving heart. In order to test the electrical effects of the global resynchronization pacing, entire ventricular pacing was transferred in cycle length by 280 ms through the epicardial mesh of the control (n=8). Surface electrograms over limb lead was shown as narrow QRS complex during the global resynchronization pacing through the epicardial mesh in comparison with wide QRS complex by RV apical pacing (FIGS. 5d and 5l). The QRS complex duration in the epicardial mesh pacing is almost the same as sinus rhythm (28.5±0.7 ms mesh pacing vs. 28.6±0.7 ms sinus rhythm, p>0.05; FIG. 5l), and significantly short in comparison with the RV apex pacing (43.5±0.98 ms; FIG. 5l). This result indicates that the entire transfer time by the global resynchronization pacing is almost the same as that by His-Purkinje transfer system.

Figure 5F:
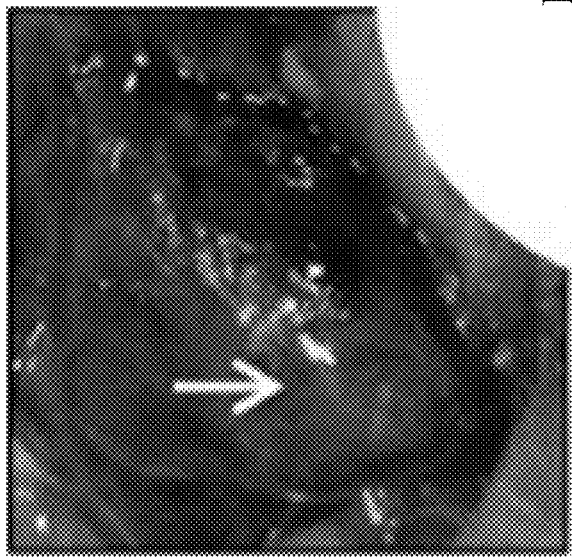
Figure 5G:
Figure 5H:
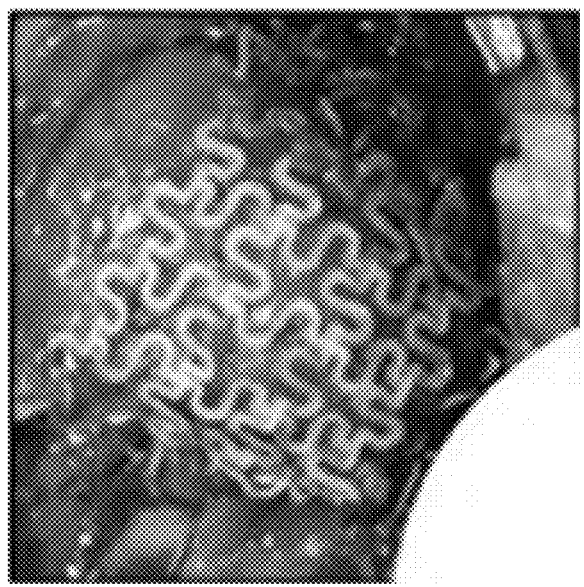
Figure 5I:
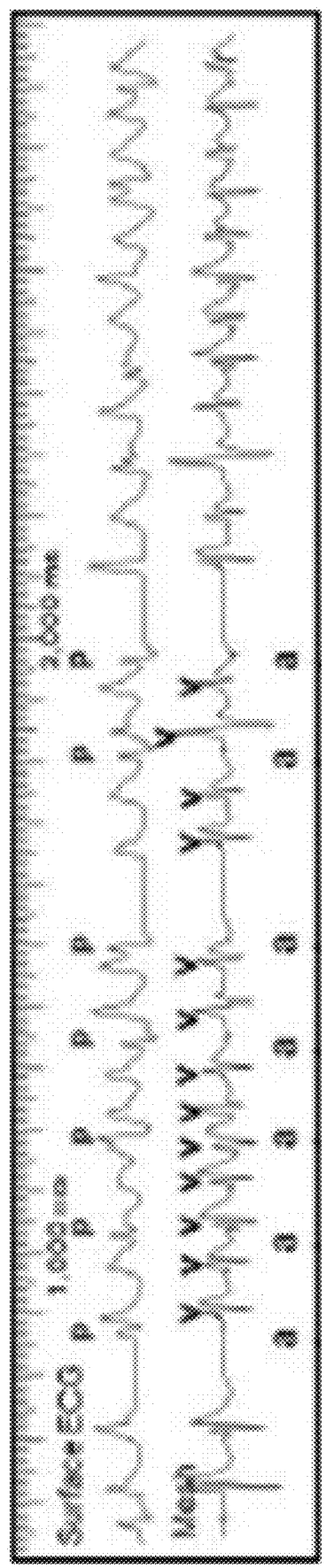
Figure 5J:
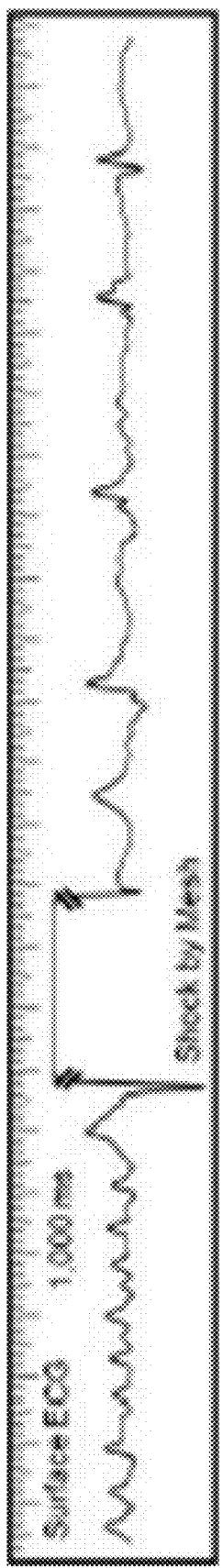
Figure 5K:
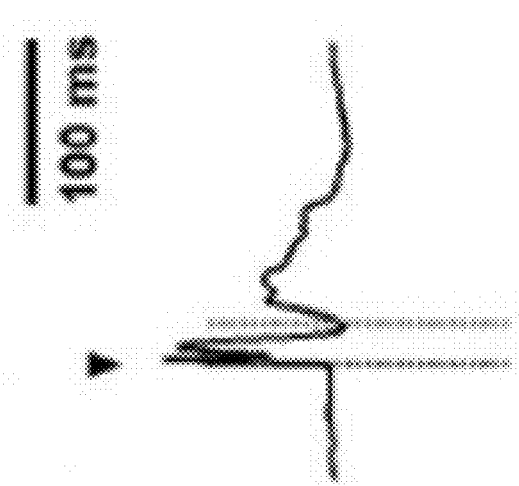
Figure 5K:
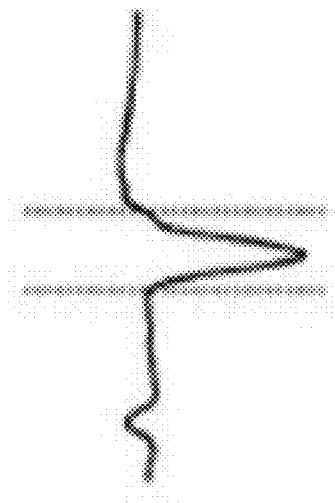
Figure 5I:
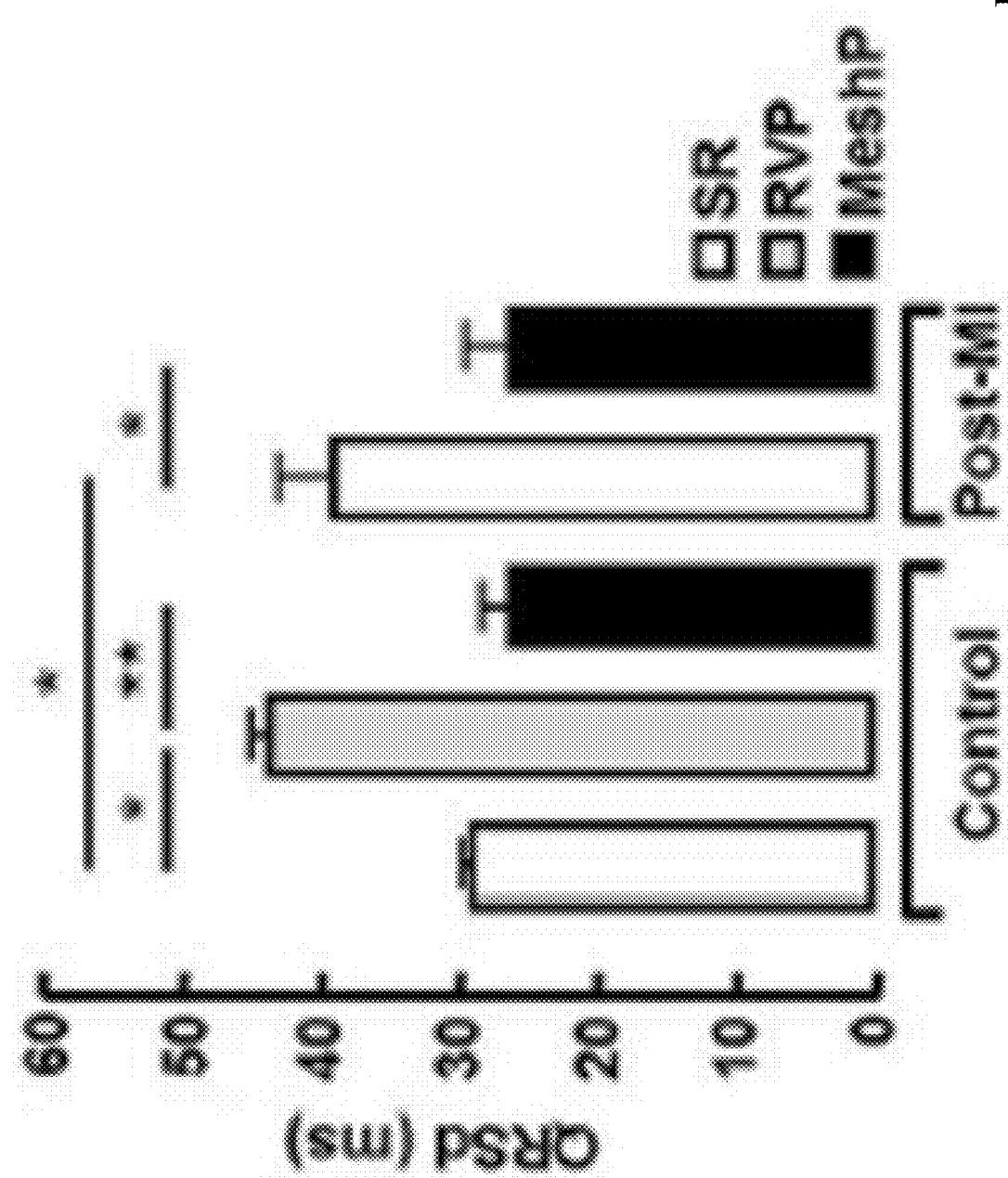
Figure 5M:
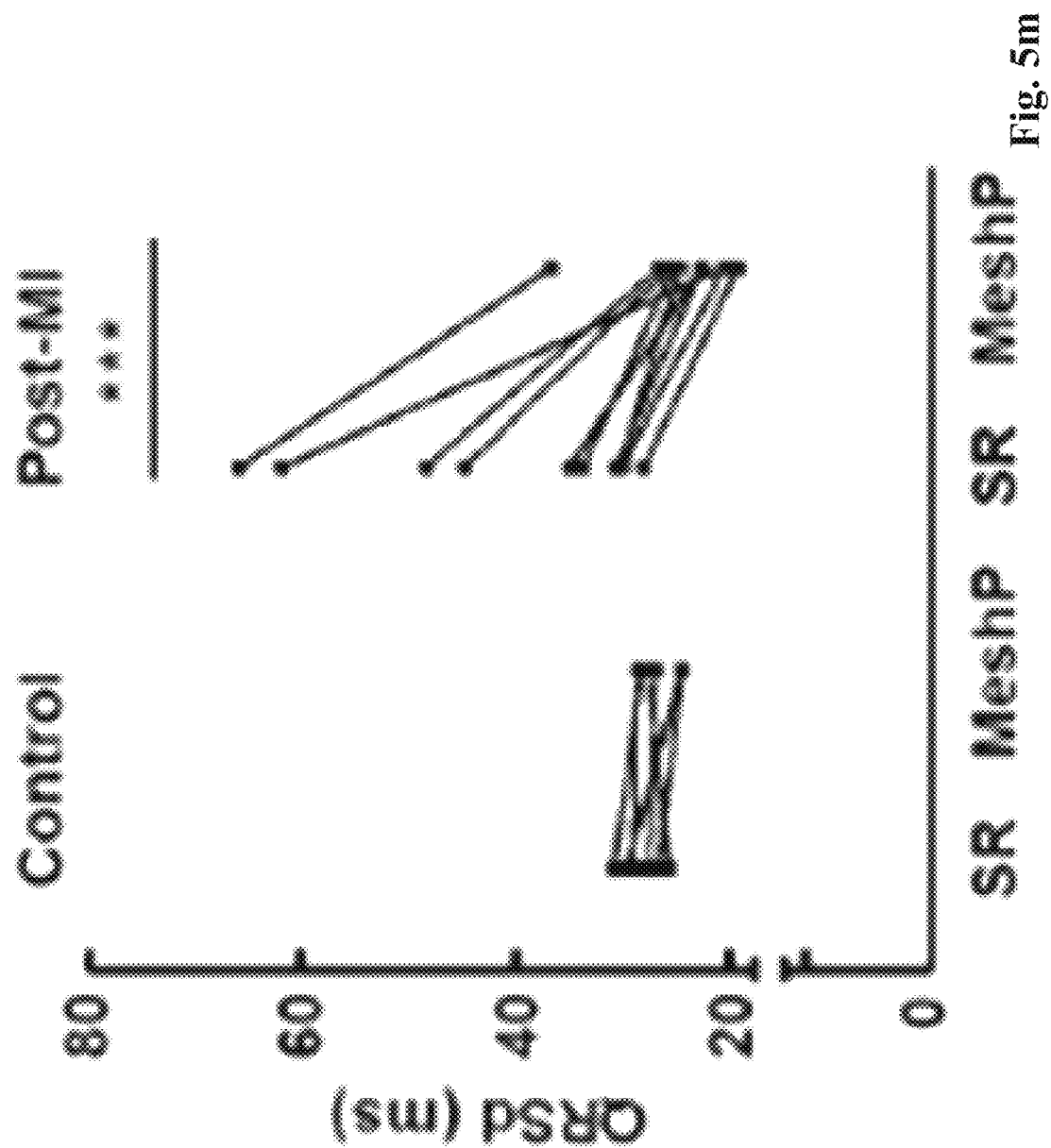

Next, since MI is the most common cause of human heart failure, we, inventors evaluated the epicardial mesh pacing in post MI rat model. After conducting left anterior descending artery ligation to 36 rats in order to induce an MI, only 19 rats (53%) in 36 rats survived 8 weeks later. At that time, sternotomy was performed to transplant the epicardial mesh (FIGS. 5f and 5h). FIGS. 5f and 5h show representative examples of the infarction part of the epicardial mesh covering 8-week post-MI heart and both ventricles. In the post-MI heart, Masson's trichrome histology showed scar lesion well-demarcated in boundary (FIG. 5g). Average QRS duration during intrinsic rhythm reflecting the damage of transfer system and myocardium by MI was significantly extended in comparison with the control heart (n=12; p<0.05; FIG. 5l). The important point is that the global resynchronization pacing through the epicardial mesh in post-MI heart causes the QRS duration similar to that observed in the control heart during the epicardial mesh pacing (FIG. 5k) reducing the QRS duration near to sinus rhythm or normality (43.9±4.8 ms intrinsic rhythm vs. 26.1±2.5 ms epicardial mesh, p<0.05; FIGS. 5*l* and 5*m*). All rats completing post-MI electrophysiological study showed normal QRS duration except animals having significantly wide QRS complex in the baseline (66 ms) of the duration reduced by 37 ms by the epicardial mesh (FIG. 5*m*). Last, the epicardial mesh demonstrated the capability to detect and terminate abnormal electrical activities such as ventricular tachycardia (VT) and ventricular fibrillation (VF), both of which occurred spontaneously in the post-MI heart (FIGS. 5*i* and 5*j*). A biphasic electrical shock of 2 J was delivered through the epicardial mesh successfully terminated ventricular fibrillation, and its potential use for both pacing and defibrillation was shown.

Figure 6A:
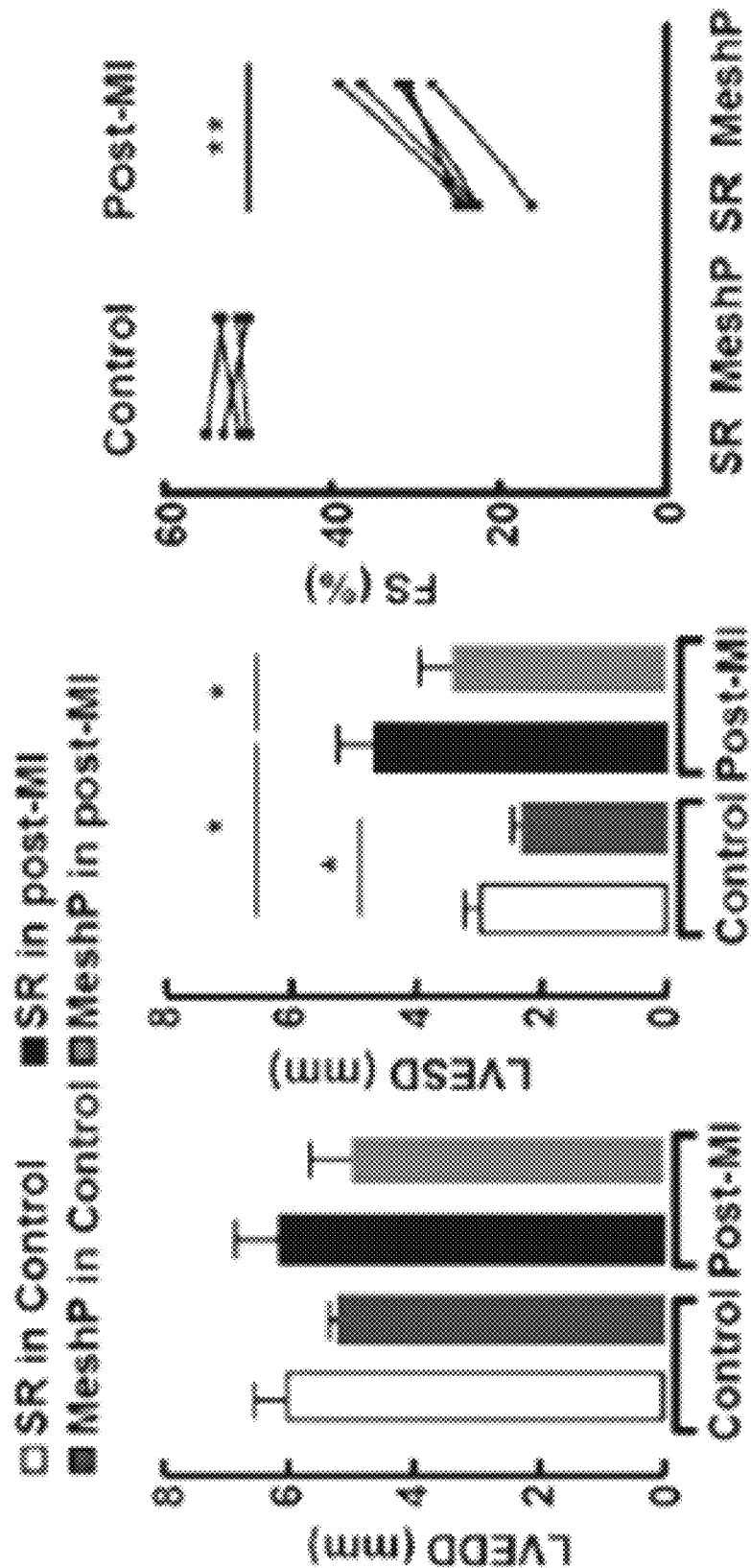
FIG. 6a shows the comparison between left ventricular end-diastolic dimension (LVEDD, left panel) and left ventricular end-systolic dimension (LVESD, middle panel) in control rats (n=5) and post-MI rats (n=6) (The epicardial mesh pacing (MeshP) was performed in 5 control rats and 5 post-MI rats. Right panel is paired comparison of fractional shortening. Statistical evaluation was performed using paired t-test. *p<0.05, **p<0.005)
Figure 6B:
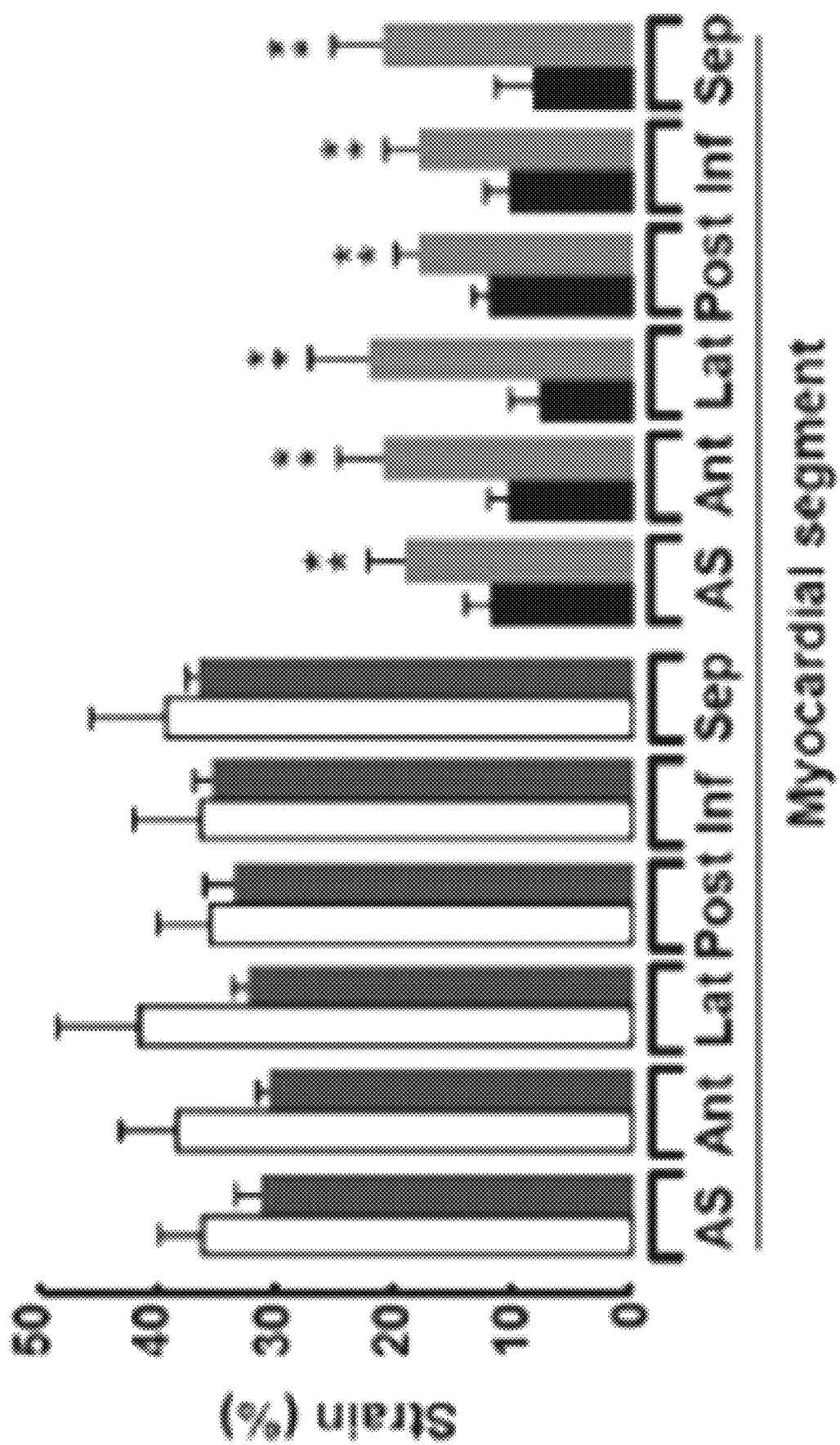
FIG. 6b is speckle tracking of strain data in control rats (n=5) and post-MI rats (n=6) (*p<0.05)

Two dimensional echocardiography was conducted for control rats (n=5/5) and post-MI rats (n=6/7). One rat died before the echocardiography, and one rat died during an operation for the epicardial mesh after the baseline echocardiography. As expected, in post-MI rats, the LV contraction function declined and the size of end-systole was larger in comparison to control rats (FIG. 6*a*). All post-MI hearts had fractional shortening (FS) of 40% or less (22.1±1.56%; FIG. 6*a*), and this guarantees that a suitable evaluation can be made for hemodynamic effects of global resynchronization therapy. Global resynchronization pacing augmented the fractional shortening to 51% in post-MI rats (FS, 33.3±1.98%), whereas there were no appreciable changes in control rats (FIG. 6*a*). To additionally evaluate individual segment of LV wall, myocardial longitudinal strain in mid-LV level during the epicardial mesh pacing was measured in control and post-MI hearts using the speckle tracking. Synchronized constrictive patterns were observed at all six mid-LV segments in control rats during global epicardial mesh pacing, whereas dyssynchronous systolic contractions were observed during RV pacing. The myocardial strain of control rats at six LV segments did not show any change by the epicardial mesh pacing with a cycle length of 280 ms (FIG. 6*b*), whereas the post-MI hearts (n=5) showed declined strains at each LV segment imagified during the same rhythm and the significant improvement of the myocardial strain during the epicardial mesh pacing (FIG. 6*b*).

Figure 6C:
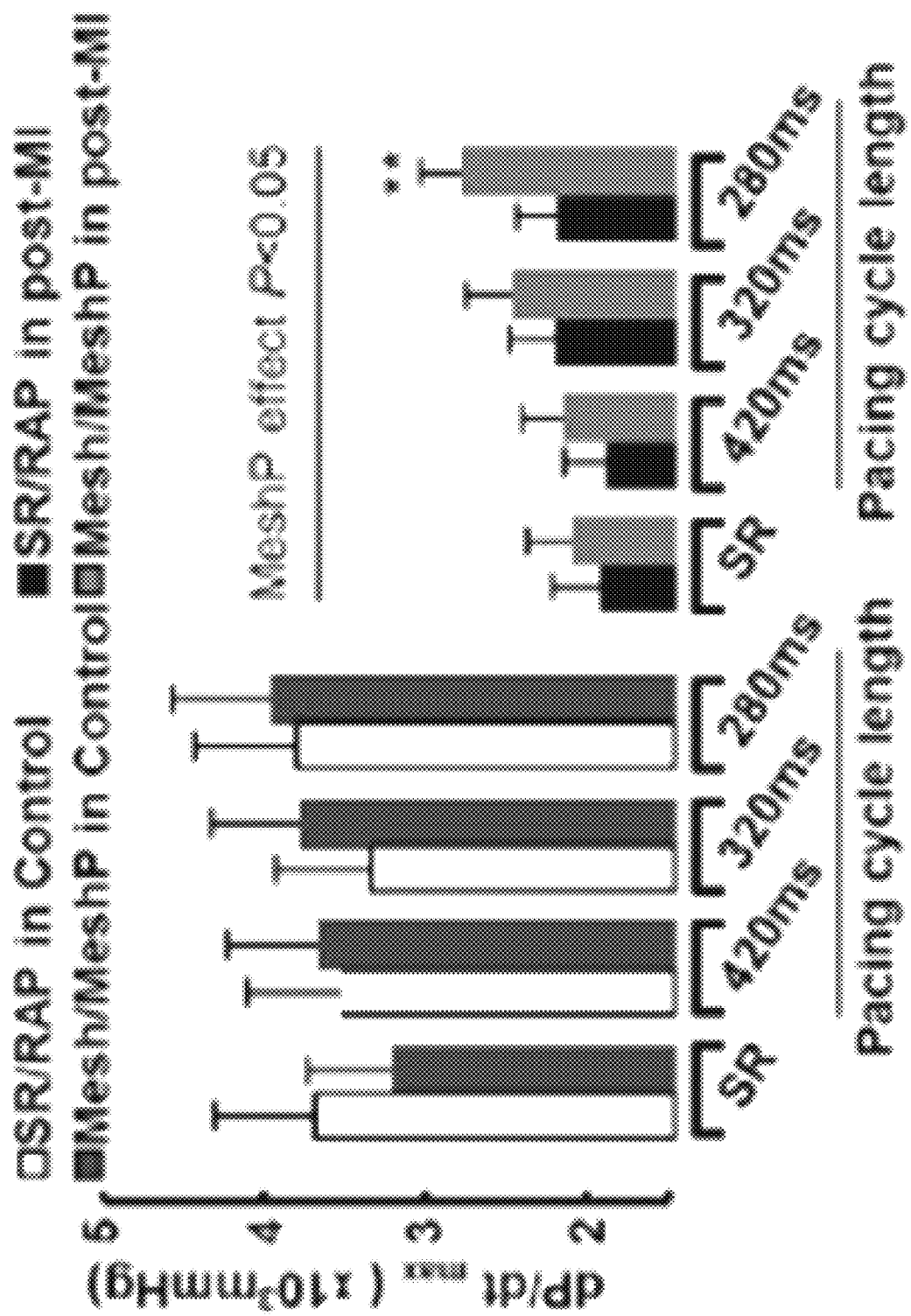
FIG. 6c shows hemodynamic effects of global resynchronization pacing ($dP/dt_{max}$) during sinus rhythm (SR), right ventricle pacing (RVP) or epicardial mesh pacing (meshP) in control rats (n=5) and post-MI rats (n=6). A rod represents statistically important difference between $dP/dt_{max}$ value in overall cycle lengths when there is the epicardial mesh pacing or when there is no epicardial mesh pacing (P<0.05 decided by using a linear mixed model). **p<0.01 between RAP and mesh pacing in the pacing cycle length of 280 ms)
Figure 6D:
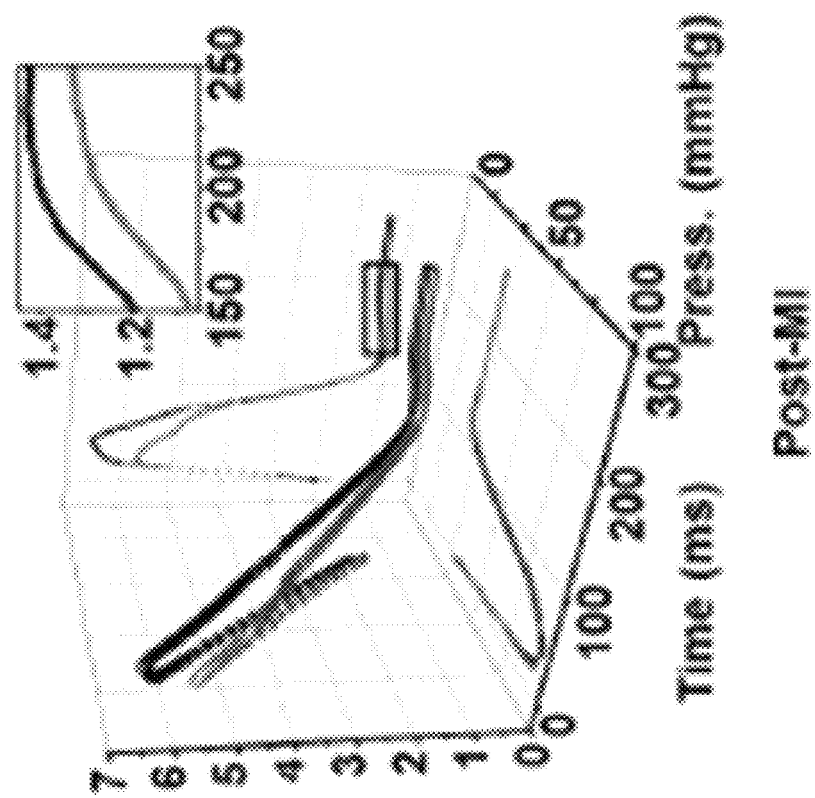
FIG. 6d is left ventricle (LV) wall stress-pressure loop during one heart cycle (LV wall stress was derived from simultaneous record of LV pressure and myocardial strain during RAP and mesh pacing at the same cycle lengths of 420 ms of post-MI rats and 280 ms of control rats)
Figure 6D:
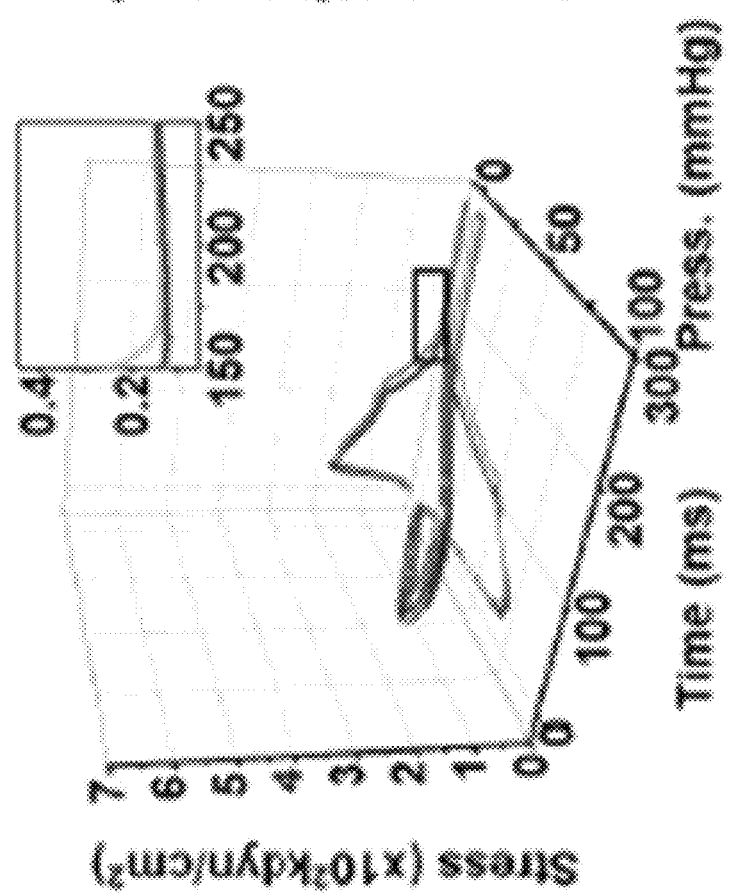
Figure 6E:
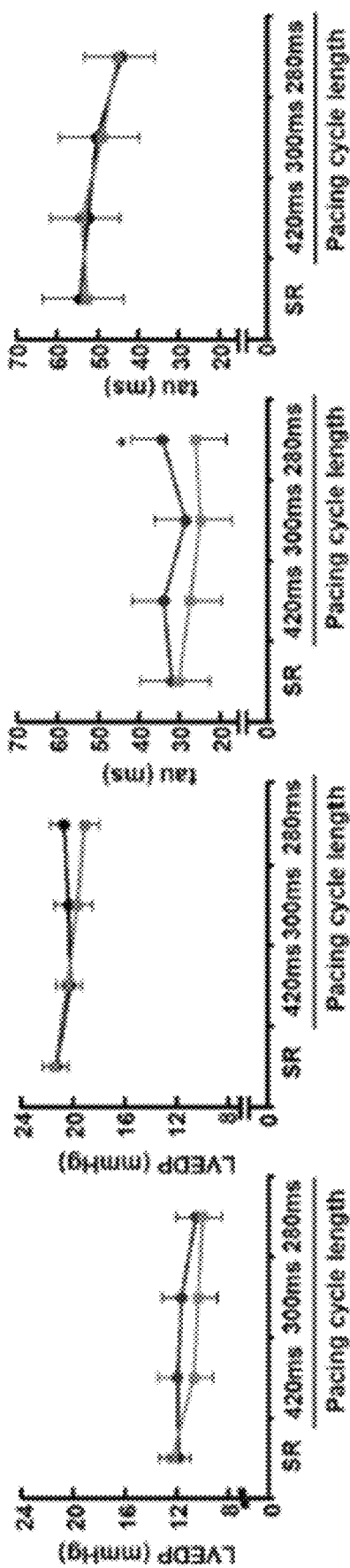
FIG. 6e shows effects on diastolic function (Under all conditions except tau at the pacing cycle length of 280 ms in control rats (n=5), any of the epicardial mesh transplant or mesh pacing did not increase a diastolic index, that is, left ventricular end-diastolic pressure (LVEDP) and tau. The epicardial mesh pacing slightly decreased LVEDP and tau, but this difference was not important in the statistics. *P<0.01).

Next, hemodynamic effects of the global resynchronization pacing using the serpentine epicardial mesh were evaluated by real time pressure monitoring of LV cavity (The volume sensor of catheter could not be used due to the interference between volume sensor and electrical pacing stimulation). In control (n=5) and post-MI rats (n=5, p>0.05 for all animals), without the pacing, the transplant of the serpentine epicardial mesh did not change significantly end-diastolic pressure and tau (diastole relaxation index) of LV (FIG. 6*e*). In comparison with control hearts, post-MI hearts exhibited the decline of LV pressure maximum rate of change falling under the parameter of the contraction function (dP/dt$_{max}$), LVEDP was improved and tau representing the disability of contraction and relaxation functions increased (FIGS. 6*c* and 6*e*). Since heart rate can influence the contraction function of LV, we, inventors made an additional evaluation for hemodynamic effects of the global resynchronization pacing in different CL (cycle length). In CL of 420 ms, 320 ms and 280 ms, the epicardial mesh pacing was compared to RV pacing where the ventricle activation occurred by intrinsic His-Purkinje transfer system. In control hearts, when comparing to RA pacing, dt$_{max}$ was similar to that during the epicardial mesh pacing in each CL (FIG. 6*c*). In post-MI hearts, the epicardial mesh pacing exhibited the improvement of average dt$_{max}$ by 2.5%, 22.5% and 31.6% in CL of 420 ms, 320 ms and 280 ms, respectively (FIG. 6*c*). These research results represent that electromechanical effects of the epicardial mesh pacing (i) are similar to electromechanical activation through health His-Purkinje transfer system in hearts and (ii) lead to improved hemodynamics in post-MI hearts.

To measure changes in wall stress, we, inventors recorded LV pressure with a Millar catheter simultaneously and measured mid-LV radial strain by echocardiography in one control heart and one post-MI heart. During the epicardial mesh pacing, the wall stress was reduced during the entire cardiac cycle (diastole and systole) in the post-MI heart, and slightly reduced in the control heart (FIG. 6*d*). In addition, we, inventors confirmed that the epicardial mesh did not influence significantly on diastole parameter including LVEDP and tau (FIG. 6*e*). The important point is that the constrictive pattern of the LV pressure was not observed in the hearts of all experimental rats.

Although the embodiments of the present invention have been disclosed for illustrative purposes, those skilled in the art will appreciate that the present invention may be embodied in other specific ways without changing the technical spirit or essential features thereof. Therefore, the embodiments disclosed in the present invention are not restrictive but are illustrative. The scope of the present invention is given by the claims, rather than the specification, and also contains all modifications within the meaning and range equivalent to the claims.

The invention claimed is:

1. An apparatus for cardiac resynchronization therapy, comprising:
   a mesh electrode that comprises:
      a first biocompatible rubber layer with a first mesh shape in which silver nanowires are substantially homogenously dispersed; and
      a portion of a second biocompatible rubber layer disposed on the first biocompatible rubber layer, the portion of the second biocompatible rubber layer having a second mesh shape, the first mesh shape being substantially the same as the second mesh shape.

2. The mesh electrode of claim 1, wherein a length of the silver nanowires ranges from 5 μm to 50 μm, and a diameter of the silver nanowires ranges from 50 nm to 150 nm.

3. The mesh electrode of claim 1, wherein the silver nanowires are ligand-exchanged silver nanowires.

4. The mesh electrode of claim 1, wherein the first biocompatible rubber is selected from a group consisting of SBS (styrene-butadiene-styrene) rubber, TPU (thermoplastic polyurethane), NBR (nitrile butadiene rubber), Hydrogel, PDMS polydimethylsiloxane), PUA (polyurethane acrylate), PVA (polyvinyl alcohol), silicone rubber, PI (polyimide), PMMA (polymethyl methacrylate), PVDF (poly(vinylidenedifluoride)).

5. The mesh electrode of claim 1, wherein a thickness of the first biocompatible rubber layer ranges from 1 μm to 500 μm.

6. The mesh electrode of claim 1, wherein the second biocompatible rubber is selected from a group consisting of SBS rubber, TPU, NBR, Hydrogel, PDMS, PUA, PVA, silicone rubber, PI, PMMA, PVDF.

7. The mesh electrode of claim 1, wherein a thickness of the second biocompatible rubber layer ranges from 1 μm to 500 μm.

* * * * *